(12) United States Patent
Giesing et al.

(10) Patent No.: US 7,993,826 B2
(45) Date of Patent: Aug. 9, 2011

(54) METHOD FOR ANALYZING BLOOD FOR THE PRESENCE OF CANCER CELLS

(75) Inventors: Michael Giesing, Lienen (DE); Bernhard Suchy, Recklinghausen (DE)

(73) Assignee: Michael Giesing, Lienen (DE)

( * ) Notice: Subject to any disclaimer, the term of this patent is extended or adjusted under 35 U.S.C. 154(b) by 630 days.

(21) Appl. No.: 10/525,019

(22) PCT Filed: Aug. 20, 2003

(86) PCT No.: PCT/EP03/09229
§ 371 (c)(1),
(2), (4) Date: Jun. 28, 2005

(87) PCT Pub. No.: WO2004/019037
PCT Pub. Date: Mar. 4, 2004

(65) Prior Publication Data
US 2006/0088840 A1 Apr. 27, 2006

(30) Foreign Application Priority Data
Aug. 20, 2002 (DE) .................................. 102 38 046

(51) Int. Cl.
C12Q 1/68 (2006.01)
C12P 19/34 (2006.01)
C07H 21/02 (2006.01)
C07H 21/04 (2006.01)

(52) U.S. Cl. .......... 435/6; 435/91.2; 536/24.3; 536/23.5

(58) Field of Classification Search ........................ None
See application file for complete search history.

(56) References Cited

U.S. PATENT DOCUMENTS

| 5,246,847 A | 9/1993 | Hartman et al. |
| 5,260,204 A | 11/1993 | Heckl et al. |
| 5,985,633 A | 11/1999 | Nick et al. |
| 2001/0051344 A1* | 12/2001 | Shalon et al. ..................... 435/6 |
| 2003/0157581 A1 | 8/2003 | Grill et al. |

FOREIGN PATENT DOCUMENTS

| CA | 2301962 | 3/1999 |
| CA | 2338751 | 2/2000 |
| DE | 100 54 632 A1 | 5/2002 |
| WO | WO 96/29430 | 9/1996 |
| WO | WO 02/18634 A2 | 3/2002 |

OTHER PUBLICATIONS

Boer et al. Identification and classification of differentially expressed genes in renal cell carcinoma by expression profiling on a global human 31,500-element cDNA array. Genome Research, vol. 11, No. 11, pp. 1861-1870, 2001.*
Entry for 1.15.1.1, printed from http://us/expasy.org/enzyme on May 5, 2008.*
Pusztai and Hess. Clinical trial design for microarray predictive marker discovery and assessment. Annals of Oncology, vol. 15, pp. 1731-1737, 2004.*
Kroese et al. Genetic tests and their evaluation: Can we answer the key questions? Genetics in Medicine, vol. 6, pp. 475-480, 2004.*
Golub et al. Molecular classification of cancer: Class discovery and class predictaion by gene expression monitoring. Science, Bol. 286, pp. 531-537, Oct. 1999.*
Entrez Gene entry for SOD2 [*Homo sapeins*], printed from http://www.ncbi.nlm.nih.gov/sites/entrez?db=gene on May 5, 2008.*
Entrez Gene entry for TXNRD1 [*Homo sapiens*], printed from http://www.ncbi.nlm.nih.gov/sites/entrez?db=gene on May 5, 2008.*
Entrez Gene entry for GPX1 [*Homo sapiens*], printed from http://www.ncbi.nlm.nih.gov/sites/entrez?db=gene on May 5, 2008.*
Seven et al. Evaluation of oxidative stress parameters in blood of patients with laryngeal carcinoma. Clinical Biochemistry, vol. 32, No. 5, pp. 369-373, 1999.*
Kizaki et al. Regulation of manganese superoxide dismutase and other antioxidant genes in normal and leukemic hematopoietic cells and their relationship to cytotoxicity by tumor necrosis factor. Blood, vol. 82, No. 4, pp. 1142-1150, Aug. 1993.*
GEO entry for platform GPL10, description and entry for thioredoxin reductase only, printed from http://www.ncbi.nlm.nih.gov/geo/ on Apr. 29, 2008.*
Giesing et al. Clinical utility of antioxidant gene expression levels in circulating cancer cell clusters for the detection of prostate cancer in patients with prostate-specific antigen levels of 4-10 ng/mL and disease prognostication after radical prostatectomy BJU International, DOI:10.1111/j.1464-410X.2009.08920.x , published online Oct. 10, 2009.*
Sarto, C., et al., "Modified Expression of Plasma Glutathione Peroxidase and Manganese Suieroxide Dismutase in Human Renal Cell Carcinoma", Electrophoresis 1999, 20, 3458-3466.
Mork, H., et al., "Inverse mRNA Expression of the Selenocysteine-Containing Proteins GI-GPx and SeP Colorectal Adenomas Compared With Adjacent Normal Mucosa", Nutrition and Cancer, 37(1), 108-116, 2000.
Sarto, C., et al., "Renal Cell Carcinoma and Normal Kidney Protein Expression", Electrophoresis 1997, 18, 599-604.
Gladyshev, V.N., et al., "Contrasting Patterns of Regulation of the Antioxidant Selenoproteins, Thioredoxin Reductase, and Glutathione Peroxidase, in Cancer Cells", Biochemical and Biophysical Research Communications, 251, 488-493 (1998) Article No. RC989495.
Bravard, A., et al., "Modifications of the Antioxidant Enzymes in Relation to Chromosome Imbalances in Human Melanoma Cell Lines", Melanoma Research 1998, 8, pp. 329-335.

(Continued)

*Primary Examiner* — Jennifer Dunston
(74) *Attorney, Agent, or Firm* — Bacon & Thomas, PLLC

(57) ABSTRACT

The present invention relates to a method for investigating body fluids for cancer cells, the use thereof and corresponding analysis kits, and the possibilities for cancer treatment derived therefrom. The method is based essentially on determining the expression of the manganese superoxide dismutase, thioredoxin reductase and/or glutathione peroxidase genes. Use of this method permits in particular reliable tumor diagnosis and prognosis. Diminishing an elevated expression of these genes has therapeutic value and may be utilized for cancer treatment.

7 Claims, 1 Drawing Sheet

OTHER PUBLICATIONS

Peskin, A. V., et al., "Superoxide Dismutase and Glutathione Peroxidase Activities in Tumors", FEBS Letters, vol. 78, No. 1, Jun. 1977, 41-45.

Kahlos, K., et al., "Manganese Superoxide Dismutase in Healthy Human Pleural Mesothelium and in Malignant Pleural Mesothelioma", Am. J. Respir. Cell Mol. Biol., vol. 18, pp. 570-580, 1998.

Dvorakova, K., "Molecular and Celular Characterization of Imexon-Resistant RPMI8226/I Myeloma Cells[1]", Molecular Cancer Therapeutics, vol. 1, p. 185-195, Jan. 2002.

Asikainen, T.M., et al., "Expression and Developmental Profile of Antioxidant Enzymes in Human Lung and Liver", A. J. Respir. Cell Mol. Biol., vol. 19, pp. 942-949, 1998.

Li, Z., et al., "Genes Regulated in Human Breast Cancer Cells Overexpressing Manganese-Containing Superoxide Dismutase", Free Radical Biology & Medicine, vol. 30, No. 3, pp. 260-267, 2001.

Mercatante, K.R., et al., "Control of Alternative Splicing by Antisense Oligonucleotides as a Potential Chemotherapy: Effects on Gene Expression", Biochem & Biophys Acta, Jul. 18, 2002, 1587 (2-3): 126-132.

Janssen, AML, et al., "Superoxide Dismutases in Relation to the Overall Survival of Colorectal Cancer Patients", British Journal of Cancer (1998) 78(8), 1051-1057.

Janseen, AML, et al., "Superoxide Dismutases in Gastric and Esophageal Cancer and the Prognostic Impact in Gastric Cancer[1]", Clinical Cancer Research, vol. 6, 3183, Aug. 2000.

Ria, F., et al., "The Level of Manganese Superoxide Dismutase Content is an Independent Prognostic Factor for Glioblastoma Biological Mechanisms and Clinical Implications", British Journal of Cancer (2001) 84(4), 529-534.

Giesing, M., et al., "Independent Prognostication and Therapy Monitoring of Breast Cancer Patients by DNA/RNA typing of Minimal Residual Cancer Cells", The International Journal of Biological Markers, vol. 15, No. 1, pp. 94-99, 2000.

Barra, D., et al., "The Primary Structure of Human Liver Manganese Superoxide Dismutase", The Journal of Biological Chemistry, vol. 259, No. 20, Issue of Oct. 25, 12595-12601, 1984.

"GeneChip® Human Genome U133 Set, Comprehensive Coverage of All Well-Substantiated Genes in the Human Genome", Gene Expression Monitoring, Affymetrix, printed Jan. 21, 2002, pp. 1-2.

Stoehlmacher, J., et al, "The -9 Ala/-9Val polymorphism in the mitochondrial targeting sequence of the manganese superoxide dismutase gene (MnSOD) is associated with age among Hispanics with colorectal carcinoma", Oncol. Rep., Mar.-Apr. 2002, 9(2):235-8 (Abstract).

Forsberg, L., et al., "Low yield of polymorphisms from EST blast searching: analysis of genes related to oxidative stress and verification of the P197L polymorphism in GPX1", Hum. Mutat. 1999, 13(4):294-300 (Abstract).

Li, S., et al., "The Role of Cellular Glutathione Peroxidase Redox Regulation in the Suppression of Tumor Cell Growth by Manganese Superoxide Dismutase[1]", Cancer Research 60, 3927-3939, Jul. 15, 2000 (Abstract).

Soderberg, A., et al., "Thioredoxin Reductase, a Redox-active Selenoprotein, Is Secreted by Normal and Neoplastic Cells: Presence in Human Plasma[1]", Cancer Research 60, 2281-2289, Apr. 15, 2000 (Abstract).

Becker, K., et al. "Thioredoxin reductase as a pathophysiological factor and drug target", Eur. J. Biochem. 267, 6118-6125 (2000) (Abstract).

Soini, Y., et al., "MnSOD expression is less frequent in tumour cells of invasive breast carcinomas than in in situ carcinomas or non-neoplastic breast epithelial cells", J. Pathol. Sep. 2001, 195(2):156-62 (Abstract).

Chung-Man, H.J., et al., "Differential expression of manganese superoxide dismutase and catalase in lung cancer", Cancer Res 2001, Dec. 1, 61(23):8578-85 (Abstract).

Janssen, A.M., et al., "Superoxide dismutases in the human colorectal cancer sequence", J. Cancer Res. Clin. Oncol., 1999, 125(6):327-35 (Abstract).

Oberley, L.W., "Anticancer therapy by overexpression of superoxide dismutase", Antioxid Redox Signal, Jun. 2001, 3(3):461-72 (Abstract).

Suzuki, K., et al., "Genistein, a soy isoflavone, induces glutathione peroxidase in the human prostate cancer cell lines LNCaP and PC-3", Int. J. Cancer 2002, Jun. 20, 99(6):846-52 (Abstract).

* cited by examiner

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial
<220> FEATURE:
<223> OTHER INFORMATION: forward primer (MNSOD)

<400> SEQUENCE: 1
gtcaccgagg agaagtacca gg                                            22

<210> SEQ ID NO 2
<211> LENGTH: 20
<212> TYPE: DNA
<213> ORGANISM: Artificial
<220> FEATURE:
<223> OTHER INFORMATION: reverse primer (MNSOD)

<400> SEQUENCE: 2
gggctgaggt ttgtccagaa                                               20

<210> SEQ ID NO 3
<211> LENGTH: 27
<212> TYPE: DNA
<213> ORGANISM: Artificial
<220> FEATURE:
<223> OTHER INFORMATION: probe (MNSOD)
```

<400> SEQUENCE: 3
cgttggccaa gggagatgtt acagccc                                    27

<210> SEQ ID NO 4
<211> LENGTH: 23
<212> TYPE: DNA
<213> ORGANISM: Artificial
<220> FEATURE:
<223> OTHER INFORMATION: forward primer (TXNRD1)

<400> SEQUENCE: 4
ggagggcaga cttcaaaagc tac                                        23

<210> SEQ ID NO 5
<211> LENGTH: 22
<212> TYPE: DNA
<213> ORGANISM: Artificial
<220> FEATURE:
<223> OTHER INFORMATION: reverse primer (TXNRD1)

<400> SEQUENCE: 5
acaaagtcca ggaccatcac ct                                         22

<210> SEQ ID NO 6
<211> LENGTH: 26
<212> TYPE: DNA
<213> ORGANISM: Artificial
<220> FEATURE:
<223> OTHER INFORMATION: probe (TXNRD1)

<400> SEQUENCE: 6
ttgggctgcc tccttagcag ctgcca                                     26

<210> SEQ ID NO 7
<211> LENGTH: 17
<212> TYPE: DNA
<213> ORGANISM: Artificial
<220> FEATURE:
<223> OTHER INFORMATION: forward primer (GPX1)

<400> SEQUENCE: 7
ctcggcttcc cgtgcaa                                               17

<210> SEQ ID NO 8
<211> LENGTH: 19
<212> TYPE: DNA
<213> ORGANISM: Artificial
<220> FEATURE:
<223> OTHER INFORMATION: reverse primer (GPX1)

<400> SEQUENCE: 8
tgaagttggg ctcgaaccc                                             19

<210> SEQ ID NO 9
<211> LENGTH: 28
<212> TYPE: DNA
<213> ORGANISM: Artificial
<220> FEATURE:
<223> OTHER INFORMATION: probe (GPX1)

<400> SEQUENCE: 9
agtttgggca tcaggagaac gccaagaa                                   28

<210> SEQ ID NO 10
<211> LENGTH: 19
<212> TYPE: DNA

```
<213> ORGANISM: Artificial
<220> FEATURE:
<223> OTHER INFORMATION: forward primer (GAPDH)

<400> SEQUENCE: 10
tgctgatgcc cccatgttc                                                   19

<210> SEQ ID NO 11
<211> LENGTH: 20
<212> TYPE: DNA
<213> ORGANISM: Artificial
<220> FEATURE:
<223> OTHER INFORMATION: reverse primer (GAPDH)

<400> SEQUENCE: 11
ggcagtgatg gcatggactg                                                  20

<210> SEQ ID NO 12
<211> LENGTH: 27
<212> TYPE: DNA
<213> ORGANISM: Artificial
<220> FEATURE:
<223> OTHER INFORMATION: probe (GAPDH)

<400> SEQUENCE: 12
tcaagatcat cagcaatgcc tcctgca                                          27

<210> SEQ ID NO 13
<211> LENGTH: 222
<212> TYPE: PRT
<213> ORGANISM: Homo sapiens

<400> SEQUENCE: 13
```

Met Leu Ser Arg Ala Val Cys Gly Thr Ser Arg Gln Leu Ala Pro Ala
1               5                  10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Thr Ala Leu Gln Pro Ala Leu Lys Phe Asn Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys

<210> SEQ ID NO 14
<211> LENGTH: 976
<212> TYPE: DNA
<213> ORGANISM: Homo sapiens

<400> SEQUENCE: 14

```
gcgggcggcg caggagcggc actcgtggct gtggtggctt cggcagcggc ttcagcagat     60
cggcggcatc agcggtagca ccagcactag cagcatgttg agccgggcag tgtgcggcac    120
cagcaggcag ctggctccgg ctttgggta tctgggctcc aggcagaagc acagcctccc    180
cgacctgccc tacgactacg gcgccctgga acctcacatc aacgcgcaga tcatgcagct    240
gcaccacagc aagcaccacg cggcctacgt gaacaacctg aacgtcaccg aggagaagta    300
ccaggaggcg ttggccaagg gagatgttac agcccagaca gctcttcagc ctgcactgaa    360
gttcaatggt ggtggtcata tcaatcatag cattttctgg acaaacctca gccctaacgg    420
tggtggagaa cccaaagggg agttgctgga agccatcaaa cgtgactttg ttcctttga    480
caagtttaag gagaagctga cggctgcatc tgttggtgtc caaggctcag gttgggttg    540
gcttggtttc aataaggaac ggggacactt acaaattgct gcttgtccaa atcaggatcc    600
actgcaagga caacaggcc ttattccact gctggggatt gatgtgtggg agcacgctta    660
ctaccttcag tataaaaatg tcaggcctga ttatctaaaa gctatttgga atgtaatcaa    720
ctgggagaat gtaactgaaa gatacatggc ttgcaaaaag taaaccacga tcgttatgct    780
gagtatgtta agctctttat gactgttttt gtagtggtat agagtactgc agaatacagt    840
aagctgctct attgtagcat tcttgatgt tgcttagtca cttatttcat aaacaactta    900
atgttctgaa taatttctta ctaaacattt tgttattggg caagtgattg aaaatagtaa    960
atgctttgtg tgattg                                                    976
```

<210> SEQ ID NO 15
<211> LENGTH: 497
<212> TYPE: PRT
<213> ORGANISM: Homo sapiens

<400> SEQUENCE: 15

Met Asn Gly Pro Glu Asp Leu Pro Lys Ser Tyr Asp Tyr Asp Leu Ile
1               5                   10                  15

Ile Ile Gly Gly Gly Ser Gly Gly Leu Ala Ala Ala Lys Glu Ala Ala
                20                  25                  30

Gln Tyr Gly Lys Lys Val Met Val Leu Asp Phe Val Thr Pro Thr Pro
            35                  40                  45

Leu Gly Thr Arg Trp Gly Leu Gly Gly Thr Cys Val Asn Val Gly Cys
        50                  55                  60

Ile Pro Lys Lys Leu Met His Gln Ala Ala Leu Leu Gly Gln Ala Leu
65                  70                  75                  80

Gln Asp Ser Arg Asn Tyr Gly Trp Lys Val Glu Glu Thr Val Lys His
                85                  90                  95

Asp Trp Asp Arg Met Ile Glu Ala Val Gln Asn His Ile Gly Ser Leu
            100                 105                 110

Asn Trp Gly Tyr Arg Val Ala Leu Arg Glu Lys Lys Val Val Tyr Glu
        115                 120                 125

Asn Ala Tyr Gly Gln Phe Ile Gly Pro His Arg Ile Lys Ala Thr Asn
    130                 135                 140

Asn Lys Gly Lys Glu Lys Ile Tyr Ser Ala Glu Ser Phe Leu Ile Ala

```
            145                 150                 155                 160

Thr Gly Glu Arg Pro Arg Tyr Leu Gly Ile Pro Gly Asp Lys Glu Tyr
                        165                 170                 175

Cys Ile Ser Ser Asp Leu Phe Ser Leu Pro Tyr Cys Pro Gly Lys
                    180                 185                 190

Thr Leu Val Val Gly Ala Ser Tyr Val Ala Leu Glu Cys Ala Gly Phe
                195                 200                 205

Leu Ala Gly Ile Gly Leu Gly Val Thr Val Met Val Arg Ser Ile Leu
            210                 215                 220

Leu Arg Gly Phe Asp Gln Asp Met Ala Asn Lys Ile Gly Glu His Met
        225                 230                 235                 240

Glu Glu His Gly Ile Lys Phe Ile Arg Gln Phe Val Pro Ile Lys Val
                        245                 250                 255

Glu Gln Ile Glu Ala Gly Thr Pro Gly Arg Leu Arg Val Val Ala Gln
                    260                 265                 270

Ser Thr Asn Ser Glu Glu Ile Ile Glu Gly Tyr Asn Thr Val Met
                275                 280                 285

Leu Ala Ile Gly Arg Asp Ala Cys Thr Arg Lys Ile Gly Leu Glu Thr
            290                 295                 300

Val Gly Val Lys Ile Asn Glu Lys Thr Gly Lys Ile Pro Val Thr Asp
        305                 310                 315                 320

Glu Glu Gln Thr Asn Val Pro Tyr Ile Tyr Ala Ile Gly Asp Ile Leu
                        325                 330                 335

Glu Asp Lys Val Glu Leu Thr Pro Val Ala Ile Gln Ala Gly Arg Leu
                    340                 345                 350

Leu Ala Gln Arg Leu Tyr Ala Gly Ser Thr Val Lys Cys Asp Tyr Glu
                355                 360                 365

Asn Val Pro Thr Thr Val Phe Thr Pro Leu Glu Tyr Gly Ala Cys Gly
            370                 375                 380

Leu Ser Glu Glu Lys Ala Val Glu Lys Phe Gly Glu Asn Ile Glu
        385                 390                 395                 400

Val Tyr His Ser Tyr Phe Trp Pro Leu Glu Trp Thr Ile Pro Ser Arg
                        405                 410                 415

Asp Asn Asn Lys Cys Tyr Ala Lys Ile Ile Cys Asn Thr Lys Asp Asn
                    420                 425                 430

Glu Arg Val Val Gly Phe His Val Leu Gly Pro Asn Ala Gly Glu Val
                435                 440                 445

Thr Gln Gly Phe Ala Ala Ala Leu Lys Cys Gly Leu Thr Lys Lys Gln
            450                 455                 460

Leu Asp Ser Thr Ile Gly Ile His Pro Val Cys Ala Glu Val Phe Thr
        465                 470                 475                 480

Thr Leu Ser Val Thr Lys Arg Ser Gly Ala Ser Ile Leu Gln Ala Gly
                        485                 490                 495

Cys

<210> SEQ ID NO 16
<211> LENGTH: 1314
<212> TYPE: DNA
<213> ORGANISM: Homo sapiens

<400> SEQUENCE: 16
gaattcgggt ggagtcctga aggagggcct gatgtcttca tcattctcaa attcttgtaa      60
gctctgcgtc gggtgaaacc agacaaagcc gcgagcccag ggatgggagc acgcggggga     120
cggcctgccg gcggggacga cagcattgcg cctgggtgca gcagtgtgcg tctcggggaa     180
```

-continued

```
gggaagatat tttaaggcgt gtctgagcag acggggaggc ttttccaaac ccaggcagct    240
tcgtggcgtg tgcggtttcg acccggtcac acaaagcttc agcatgtcat gtgaggacgg    300
tcgggccctg aaaggaacgc tctcggaatt ggccgcggaa accgatctgc ccgttgtgtt    360
tgtgaaacag agaaagatag gcggccatgg tccaaccttg aaggcttatc aggagggcag    420
acttcaaaag ctactaaaaa tgaacggccc tgaagatctt cccaagtcct atgactatga    480
ccttatcatc attggaggtg gctcaggagg tctggcagct gctaaggagg cagcccaata    540
tggcaagaag gtgatggtcc tggactttgt cactcccacc cctcttggaa ctagatgggg    600
tcttggagga acatgtgtga atgtgggttg catacctaaa aaactgatgc atcaagcagc    660
tttgttagga caagccctgc aagactctcg aaattatgga tggaaagtcg aggagacagt    720
taagcatgat tgggacagaa tgatagaagc tgtacagaat cacattggct ctttgaattg    780
gggctaccga gtagctctgc gggagaaaaa agtcgtctat gagaatgctt atgggcaatt    840
tattggtcct cacaggatta aggcaacaaa taataaaggc aaagaaaaaa tttattcagc    900
agagagtttt ctcattgcca ctggtgaaag accacgttac ttgggcatcc ctggtgacaa    960
agaatactgc atcagcagtg atgatctttt ctccttgcct tactgcccgg gtaagaccct   1020
ggttgttgga gcatcctatg tcgctttgga gtgcgctgga tttcttgctg gtattggttt   1080
aggcgtcact gttatggtta ggtccattct tcttagagga tttgaccagg acatggccaa   1140
caaaattggt gaacacatgg aagaacatgg catcaagttt ataagacagt tcgtaccaat   1200
taaagttgaa caaattgaag cagggacacc aggccgactc agagtagtag ctcagtccac   1260
caatagtgag gaaatcattg aaggagaata taatacggtg atgctggcaa tagg          1314
```

<210> SEQ ID NO 17
<211> LENGTH: 201
<212> TYPE: PRT
<213> ORGANISM: Homo sapiens

<400> SEQUENCE: 17

```
Met Cys Ala Ala Arg Leu Ala Ala Ala Ala Gln Ser Val Tyr Ala
1               5                   10                  15

Phe Ser Ala Arg Pro Leu Ala Gly Gly Glu Pro Val Ser Leu Gly Ser
                20                  25                  30

Leu Arg Gly Lys Val Leu Leu Ile Glu Asn Val Ala Ser Leu Cys Gly
            35                  40                  45

Thr Thr Val Arg Asp Tyr Thr Gln Met Asn Glu Leu Gln Arg Arg Leu
        50                  55                  60

Gly Pro Arg Gly Leu Val Val Leu Gly Phe Pro Cys Asn Gln Phe Gly
65                  70                  75                  80

His Gln Glu Asn Ala Lys Asn Glu Glu Ile Leu Asn Ser Leu Lys Tyr
                85                  90                  95

Val Arg Pro Gly Gly Gly Phe Glu Pro Asn Phe Met Leu Phe Glu Lys
            100                 105                 110

Cys Glu Val Asn Gly Ala Gly Ala His Pro Leu Phe Ala Phe Leu Arg
        115                 120                 125

Glu Ala Leu Pro Ala Pro Ser Asp Asp Ala Thr Ala Leu Met Thr Asp
    130                 135                 140

Pro Lys Leu Ile Thr Trp Ser Pro Val Cys Arg Asn Asp Val Ala Trp
145                 150                 155                 160

Asn Phe Glu Lys Phe Leu Val Gly Pro Asp Gly Val Pro Leu Arg Arg
                165                 170                 175
```

```
Tyr Ser Arg Arg Phe Gln Thr Ile Asp Ile Glu Pro Asp Ile Glu Ala
        180                 185                 190

Leu Leu Ser Gln Gly Pro Ser Cys Ala
        195                 200
```

<210> SEQ ID NO 18
<211> LENGTH: 856
<212> TYPE: DNA
<213> ORGANISM: Homo sapiens

<400> SEQUENCE: 18

```
cttgttcggg gcgctccgct ggcttcttgg acaattgcgc catgtgtgct gctcggctag    60
cggcggcggc ggcccagtcg gtgtatgcct tctcggcgcg cccgttggcc ggcggggagc   120
ctgtgagcct gggctccctg cggggcaagg tactacttat cgagaatgtg cgtccctct   180
gaggcaccac ggtccgggac tacacccaga tgaacgagct gcagcggcgc tcggacccc   240
ggggcctggt ggtgctcggc ttcccgtgca accagtttgg gcatcaggag aacgccaaga   300
acgaagagat tctgaattcc ctcaagtacg tccggcctgg tggtgggttc gagcccaact   360
tcatgctctt cgagaagtgc gaggtgaacg gtgcgggggc gcccctctc ttcgccttcc   420
tgcgggaggc cctgccagct cccagcgacg acgccaccgc gcttatgacc gaccccaagc   480
tcatcacctg gtctccggtg tgtcgcaacg atgttgcctg gaactttgag aagttcctgg   540
tgggccctga cggtgtgccc ctacgcaggt acagccgccg cttccagacc attgacatcg   600
agcctgacat cgaagccctg ctgtctcaag ggcccagctg tgcctagggc gcccctccta   660
ccccggctgc ttggcagttg cagtgctgct gtctcggggg ggttttcatc tatgagggtg   720
tttcctctaa acctacgagg gaggaacacc ttgatcttac agaaaatacc acctcgagat   780
gggtgctggt cctgttgatc ccagtctctg ccagaccaag gcgagtttcc ccactaataa   840
agtgccgggt gtcagc                                                    856
```

<210> SEQ ID NO 19
<211> LENGTH: 60
<212> TYPE: DNA
<213> ORGANISM: Artificial
<220> FEATURE:
<223> OTHER INFORMATION: probe (NMSOD)

<400> SEQUENCE: 19

```
gaacaacagg ccttattcca ctgctgggga ttgatgtgtg ggagcacgct tactaccttc    60
```

<210> SEQ ID NO 20
<211> LENGTH: 60
<212> TYPE: DNA
<213> ORGANISM: Artificial
<220> FEATURE:
<223> OTHER INFORMATION: probe (TXNRD1)

<400> SEQUENCE: 20

```
cgtgttgtgg gctttcacgt actgggtcca aatgctggag aagttacaca aggctttgca    60
```

<210> SEQ ID NO 21
<211> LENGTH: 60
<212> TYPE: DNA
<213> ORGANISM: Artificial
<220> FEATURE:
<223> OTHER INFORMATION: probe (GPX2)

<400> SEQUENCE: 21

```
tacagccgca ccttcccaac catcaacatt gagcctgaca tcaagcgcct ccttaaagtt    60
```

-continued

```
<210> SEQ ID NO 22
<211> LENGTH: 60
<212> TYPE: DNA
<213> ORGANISM: Artificial
<220> FEATURE:
<223> OTHER INFORMATION: probe (GPX3)

<400> SEQUENCE: 22
ctcttctggg aacccatgaa ggttcacgac atccgctgga actttgagaa gttcctggtg     60
```

US 7,993,826 B2

METHOD FOR ANALYZING BLOOD FOR THE PRESENCE OF CANCER CELLS

CROSS-REFERENCE TO RELATED APPLICATIONS

This is a 371 of PCT/EP2003/009229, filed 20 Aug. 2003 which claims priority from German Patent Application No. 102 38 046.5 filed 20 Aug. 2002.

TECHNICAL FIELD

The present invention relates to a method for investigating body fluids for cancer cells, the use thereof and corresponding analysis kits, and the possibilities for cancer treatment derived therefrom. The method is based essentially on determining the expression of the manganese superoxide dismutase, thioredoxin reductase and/or glutathione peroxidase genes. The use of this method permits in particular reliable tumor diagnosis and prognosis. Diminishing an elevated expression of these genes may have therapeutic value and be utilized for cancer treatment.

BACKGROUND OF THE INVENTION

Aerobic organisms in particular are exposed to oxidative stress throughout life. Both endogenous and exogenous factors lead to continuous production of free radicals, especially in the form of reactive oxygen species. Without an appropriate antioxidative protection, the damage, associated with the reaction of the free radicals, to cellular constituents and cellular structures would soon result in death of the cell.

Although the organism is able to avoid most of the oxidative damage, the antioxidative protection, which is very complex and consists of several hundred components in each individual cell, does not appear to be comprehensive. Instead, it must be assumed that oxidative damage accumulates with increasing age, suggesting that this is an essential, if not the decisive, factor in the aging process. The development of cancer is also discussed in this connection.

There are at least three different superoxide dismutases (SOD for short) in human tissues. These include the cytoplasmic Cu/Zn superoxide dismutases and the mitochondrial manganese superoxide dismutase (MNSOD for short). These catalyze the decomposition of superoxide free radicals ($O_2^-$), producing hydrogen peroxide ($H_2O_2$) which can in turn be decomposed by catalases and/or glutathione peroxidases to $H_2O$ and $O_2$.

It has been possible to show that the development of colorectal tumors and hepatic metastases thereof is associated with a significant increase in MNSOD expression (Janssen et al. J. Cancer Res Clin. Oncol. 125(6), 327-35, 1999). It was also possible to show this for lung tumors (Chung-man H J, et al. Cancer Research 1; 61(23), 8578-85, 2001) and for breast cancer cells (Zhongkui Li et al., Free Radical & Medicine 30; 260-267, 2001). It was observed in clinical studies that an increased MNSOD antigen level in colorectal carcinomas, in stomach tumors and in glioblastomas is an independent prognostic factor for the reduced survival rate of the patients investigated (Janssen A M L et al. Br. J. Cancer, 78(8) 1051-1057, 1998; Janssen A M L et al. Clinical Cancer Research vol. 6., 3183-3192, 2000; Ria F. et al. British Journal of Cancer 84(4) 529-534, 2001). On the other hand, epithelial cells from carcinomas in situ of the breast and benign hyperplasias were more often found to be strongly positive for MNSOD expression than neoplastic epithelial cells from invasive carcinomas of the breast (Soini Y. et al. J Pathol Sep.195(2),156-62, 2001).

Thioredoxin reductase (TXNRD for short) is a key enzyme for regulating the intracellular redox state. This enzyme catalyzes the NADPH-dependent reduction of thioredoxin disulfide and a large number of other oxidized cellular constituents (Becker K, et al. Eur. J. Biochem. 267, 6118-6125, 2000). Constitutive expression of TXNRD has been detected in various human cell types, e.g. leukocytes. According to recent studies, TXNRD expression is thought to be involved in the development of tumors (Söderberg A. et al. Cancer Research 60, 2281-2289, 2000).

Glutathione peroxidase (GPX for short) plays an important part in protection from oxidative stress. This enzyme catalyzes the decomposition of $H_2O_2$ to $H_2O$ and $O_2$. Overexpression of GPX1 is therefore able to protect cells from oxidative destruction and appears to be important especially when MNSOD is also overexpressed, because accumulation of $H_2O_2$ is otherwise possible (Li S., et al. Cancer Research 60, 3927-3939, 2000). A reduced GPX1 expression was observed in imexonresistant RPM/8226/I myeloma cells (Dvorakova K. et al. Molecular Cancer Therapeutics 1, 185-195, 2002).

It has been possible in recent years, through the identification and characterization of disseminated cancer cells, to achieve astonishing advances in the diagnosis, prognosis and therapy of cancers. This approach is based on the realization that the disseminated cancer cells are a tumor entity independent of the primary tumor and therefore are fundamentally different from cells of the primary tumor on the basis of a different genotype and phenotype. Thus, for example, it is possible with the aid of multiparameter analyses to answer, irrespective of the status of the primary tumor, questions with prognostic and therapeutic relevance in a number of patients with breast cancer (Giesing M. et al., The International Journal of Biological Markers vol. 15 (1), 94-99, 2000.

SUMMARY OF THE INVENTION

One object of the present invention is to indicate a further practicable method permitting reliable cancer diagnosis. The method ought advantageously also to answer prognostic questions about the further course of a cancer. A further object of the present invention is to indicate targets for medical treatment of cancer.

The present invention relates to a method for investigating biological samples for cancer cells, where the expression of at least 2 genes which are selected from i) manganese superoxide dismutase genes;
ii) thioredoxin reductase genes; and
iii) glutathione peroxidase genes is determined on at least one cell-containing fraction of the biological sample.

The present invention also relates to analysis kits for carrying out the method of the invention.

DETAILED DESCRIPTION

Figure 1:
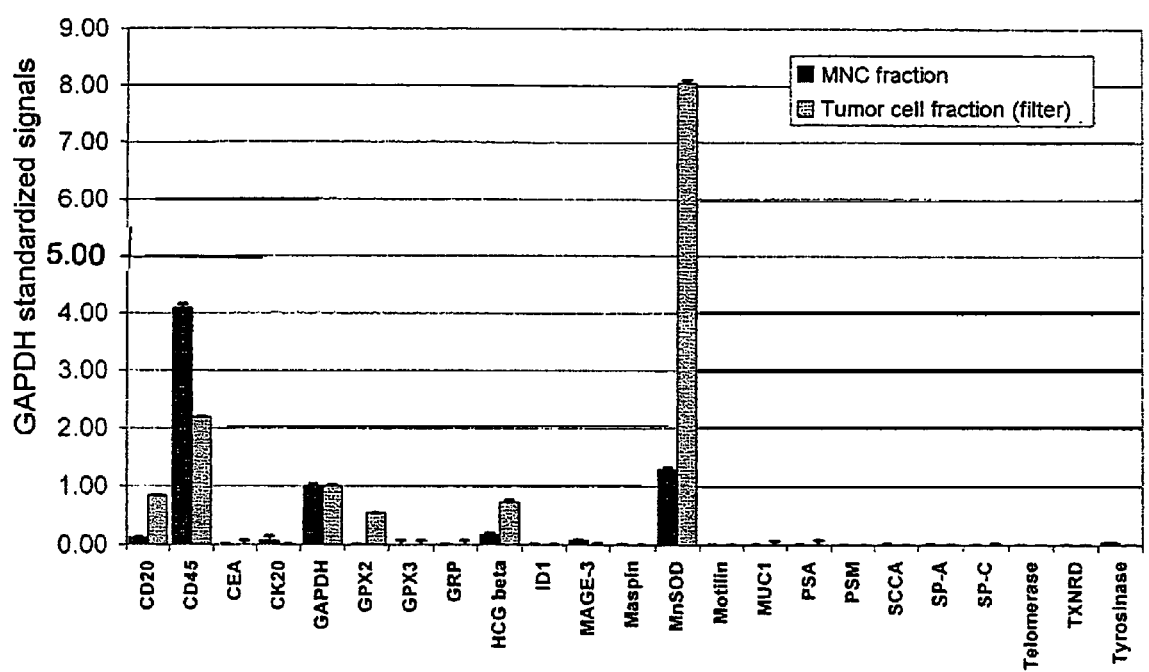
FIG. 1 shows a CCD contact exposure images generated in a detection measurement of the invention and shows results of Example 3.

The term cancer cell represents according to the invention a cell which exhibits one or more modification associated with cancer, that is dysplasia in the general sense. The basis for this definition is the idea that a continuous alteration process is involved in the development of cancer. For example, a plurality of alterations, especially in the genetic material or in the expression of the genetic material by cells is usually required-to progress from a normal cell to a cancer cell and in particular to a tumor cell. The term cancer cell therefore also includes precursors of cancer and in particular tumor cells with cancerous or tumorous modifications.

The gene expression analysis of the invention comprises determination of the expression of at least two genes (parameters). Analysis of a single parameter essentially involves three method steps:
a) expedient provision of the gene expression product to be determined;
b) quantification of the gene expression product;
c) evaluation.

Method steps a), b) and c) are advantageously carried out in the stated sequence. Investigation of a plurality of parameters can take place in separate methods or, in a preferred embodiment of the present invention, at least partly in parallel in an appropriately designed method, in which case at least method steps a) and b) are carried out in parallel for at least 2 of the parameters i), ii) and iii) of the invention.

In a particular embodiment of the method of the invention, the expression of at least one MNSOD gene is determined in combination with the expression of at least one further gene selected from thioredoxin reductase genes and glutathione peroxidase genes. Of these, the combination of MNSOD genes with TXNRD genes is preferred.

In a further particular embodiment of the method of the invention, the expression of at least one MNSOD gene, of at least one TXNRD gene and of at least one GPX gene is determined.

a) Provision of the Gene Expression Product to be Determined

The method of the invention is suitable for investigating samples of any biological origin. One embodiment relates to body samples of human and animal origin. Samples such as tissues, native, frozen, fixed, with and without dissection, blood and blood constituents or isolates thereof, further body fluids, e.g. bone marrow, lymph, sputum, lavages, puncture fluids, ascites, mucosal smears, exudates and urine, or stool, and especially cell-containing fractions thereof, can advantageously be investigated by the method of the invention. It is accordingly an in vitro method.

In a preferred embodiment of the present invention, body fluids, especially blood and blood constituents or isolates thereof, and also bone marrow, in which cancer cells are present where appropriate, are investigated. Body fluids are investigated in particular for disseminated cancer cells.

The term "disseminated cancer cell" is defined in particular in relation to solid tumors, that is to say in particular primary tumors, metastases and recurrences. In contrast to solid tumors, disseminated cancer cells are able to circulate in the body of an individual. This usually takes place via endogenous transport organs, especially body fluids, in particular blood. Disseminated cancer cells are usually derived from a solid tumor by initially being part of a solid tumor, that is in particular of the tumor tissue, from which they subsequently become detached. In this way, disseminated cancer cells leave the region of the body defined by the solid tumor, especially the morphological structural units affected by the tumor, for example the organ, and reach inter alia sites with which there is no morphological connection starting from the solid tumor.

According to a particular aspect, disseminated-cancer cells are characterized by their relatively small amount in a sample based on the non-cancer cells which are likewise present, i.e. they usually constitute a comparatively small proportion of the cellular constituents of the sample. They are therefore also referred to as residual cancer cells (minimal residual disease, MRD for short). Considering for example cell-containing body fluids, the proportion of disseminated cancer cells is usually below 1:1000, mostly below 1:10 000 and in many case even below 1:100 000, based on the number of non-cancer cells in a randomly obtained sample of the body fluid. In the case of blood, these ratios apply in particular in relation to mononuclear cells (for short: MNC).

Disseminated cancer cells are usually investigated in cell-containing mixtures which optionally comprise disseminated cancer cells in addition to non-cancer cells. The mixtures may comprise various proportions of disseminated cancer cells for the gene expression determination to be carried out according to the invention. However, proportions of at least 50% cancer cells are expedient, proportions of at least 70% are preferred and proportions of at least 80% are advantageous.

With a view to the gene expression analysis to be carried out according to the invention, if necessary a preparatory processing of the cellular constituents present in the sample, and in particular of the gene expression products to be determined, takes place, by which means the latter are provided in an expedient form in relation to the method of the invention. Such processing usually corresponds to customary practice and is based in particular on the requirements for expression determination by protein or nucleic acid analysis.

An enrichment of cancer cells, and in particular of disseminated cancer cells, going beyond this can likewise take place in a manner known per se, for example by known methods for isolating cancer cells, such as immunospecific adsorption methods, microdissection methods, density gradient methods or filtration methods.

Isolation means for the purposes of the present invention any enrichment of a constituent to be isolated from a mixture which comprises this constituent in addition to at least another one. The result of the isolation may therefore perfectly well be a further mixture which, however, comprises the constituent to be isolated in a higher concentration in relation to at least one other constituent compared with the original mixture.

According to a particular aspect, the processing of the invention takes place with enrichment of cancer cells. This aspect relates in particular to the investigation of body fluids with relatively small proportions of disseminated cancer cells, in particular those described above. The aim of this type of processing is to provide test cells or, usually, a test cell mixture which then have or has a higher proportion of cancer cells than the original cells or the original cell mixture if cancer cells are present in the original cells or in the original cell mixture. The original cells, the original cell mixture or parts thereof may serve as comparison cells or comparison cell mixture which then have or has a lower proportion of cancer cells than the test cells or the test cell mixture if cancer cells are present in the original cell mixture.

A particular method for enrichment of disseminated cancer cells is described in WO 00/06702. This method is incorporated in the present disclosure by reference. The disseminated cancer cells which can be enriched by this method are distinguished by their dedifferentiated, premetastatic character. They are therefore also referred to as micrometastases. In contrast to disseminated cancer cells which can be enriched in particular with immunospecific adsorption methods, i.e. in particular epithelial, relatively small cancer cells (especially with diameters of about 20 μm or less), the cancer cells which can be enriched by the method described in WO 00/06702 have undergone an epithelial-mesenchymal transition: they are usually larger (in particular with diameters of more than about 20 μm) and usually no longer exhibit the organotypical expression pattern and/or the epithelial expression characteristics of the disseminated cancer cells which can be enriched in particular by immunospecific adsorption methods. Thus, whereas with epithelial disseminated cancer cells there is still a certain connection to the primary tumor via the organotypical expression pattern and/or the epithelial expression characteristics, the mesenchymal disseminated cancer cells are independent of the primary tumor. This makes them into disseminated cancer cells which are preferably investigated according to the invention.

In the method described in WO 00/06702, a cell-containing body fluid or parts thereof, for example a nonspecifically enriched fraction, are passed through a screen with a mesh or pore width of about 10 to 200 μm, and the screen residue remaining on the screen, i.e. the cell fraction retained on the screen, is obtained. A proportion of cancer cells of at least 50% is achieved in the screen residue, as long as the cell-containing body fluid or parts thereof comprise cancer cells, through use of screens of particular mesh or pore size which make a size- and shape-dependent separation process possible. Screens used in the known methods are sheet-like or porous structures with orifices which have dimensions such that non-cancer cells present in the cell-containing body fluid are able to pass through, whereas cancer cells or cancer cell aggregates are retained.

In an advantageous further development of the method, which makes simple automation and standardization of the method possible, and at the same time further increases the purity of the filtered cancer cell fraction, it is possible to use a flat filter with a mesh or pore width of about 10-200 μm which is disposed in the filter housing which makes uniform rinsing through of the filter surface possible owing to a suitable fluidic design. This is described in particular in DE 100 54 632 and is incorporated in the present disclosure by reference.

Thus, in a particular embodiment, the cell-containing body fluid or parts thereof are conveyed into an inlet port of a filter housing, the body fluid is passed laterally out of the inlet port into a fluid chamber on the inlet side of the filter housing and is distributed over a flat filter disposed in the filter housing and having a mesh or pore width of about 10-200 μm essentially parallel to the surface of the flat filter, the body fluid or the parts thereof are transported over the flat filter and separated into a residue remaining on the flat filter and a filtrate, the filtrate is collected in a fluid chamber on the outlet side and is discharged through an outlet port and subsequently the residue is obtained.

If cancer cells are to be isolated from blood, it is preferred according to the invention initially to separate white blood cells by density gradient centrifugation. Cancer cells are found in particular in the fraction which also comprises mononuclear cells, so that this fraction (referred to hereinafter as MNC fraction) is preferably passed on to the subsequent filtration or alternatively to another method for isolating cancer cells.

The filtration of the cell-containing body fluid or the fraction is complete when the total cell-containing fluid has passed through the screen or the flat filter. A washing step may follow, in which further liquid, preferably buffer or culture medium, is passed through the screen or the flat filter. The washing liquid can be added to the previously obtained filtrate or else be collected separately therefrom and discarded where appropriate.

The cell fraction retained on the screen or flat filter can be passed on directly to the subsequent expression analysis or initially to storage. The residue comprising the cancer cells is advantageously initially detached from the screen or flat filter and collected. Various procedures can be chosen for this purpose depending on the nature of the subsequent use.

For example, the residue can be incubated in a solution which leads to lysis of the cells and permits cellular constituents such as nucleic acids, proteins or lipids to be obtained. It is advantageous in this case for the solution to be agitated during the incubation. If the method of the invention is carried out manually, it is possible for example to connect a syringe piston in each case to the inlet port and to the outlet port of the filtering apparatus and to pump the solution backwards and forwards between the two syringes. If the method proceeds automatically, a corresponding agitation of the solution can be achieved by conveying means such as, for example, pumps.

Vital cancer cells are obtained by dissolving the residue adhering to the flat filter, advantageously by back-flushing the filter with a liquid which is conveyed from the fluid chamber on the outlet side of the filter housing into the fluid chamber on the inlet side. The back-flushing liquid is advantageously a buffer solution or a culture medium. The cancer or tumor cells obtained in this way can for example be cultivated to obtain cellular constituents or vaccines. Alternatively, cancer cells can be detached from the filter surface using centrifugal force or by means of so-called optical tweezers.

Suitable screens or flat filters usually have a mesh or pore width of about 10-200 μm, preferably of 15 to 30 μm, particularly preferably of 17-27 μm and very particularly preferably of about 20 μm. The flat filter is advantageously designed as membrane filter, in which case typical filter materials such as plastics networks or fabrics, microporous membrane filters, filter tile or combinations thereof can be employed. Suitable filter materials and suitable methods for producing such filters are described in particular in WO 00/06702. It is particularly preferred to use filters which are made of solvent-resistant material and which may consist for example of plastics such as polyethylene, polypropylene, polytetrafluoroethylene, highly fluorinated polymers, vinylidene fluoride, aminoplastics and, in particular, polyester.

To select the screen or filter suitable in each case for isolating particular cancer cells, the skilled worker can obtain, in preliminary experiments with screens or filters of increasingly narrow mesh (for example in the sequence 200 μm, 115 μm, 74 μm, 51 μm, 38 μm, 30 μm, 27 μm, 20 μm, 17 μm, 15 μm and 10 μm), individual cell fractions and investigate them for their therapeutic and diagnostic relevance. It may also prove advantageous in this connection to employ filter combinations, i.e. in the above example for instance to filter off, using a 115 μm filter, less relevant, larger aggregates and to analyze only the cancer cell fraction collected on a downstream 20 μm filter.

The expression analysis of the invention relates to the determination of any gene expression products such as proteins or nucleic acids and, in this connection, especially mRNA and the nucleic acids which can be derived therefrom, such as cDNA. Generally known methods can be applied to obtain these gene expression products, where appropriate mixed with further cellular constituents. For nucleic acids in particular the methods and reagents known to be suitable for the area of isolating and purifying nucleic acids will be used, for example a solution comprising guanidine isothiocyanate and phenol (cf. Lottspeich F. and Zorbas H. (editors) Bioanalytik, Heidelberg; Berlin: Spektrum, Akad. Verl., 1998, in particular chapter 21). It is possible in particular for mRNA to be isolated in the form of poly A⁺ mRNA by means of oligo-dT column chromatography or correspondingly equipped magnetic beads.

b) Quantification of the Gene Expression Product

The methods which can be used to quantify the respective gene expression product are primarily governed by the nature of the gene expression product. Thus, it is possible in principle to employ all the methods known to be suitable for quantifying proteins and nucleic acids from the areas of protein analysis and nucleic acid analysis. From the area of protein analysis, mention may be made for example of enzymatic activity assays, immunological techniques, certain spectroscopic methods and mass spectrometry, if necessary in combination with chromatographic or electrophoretic separation methods. In order to ensure specific detection of the expressed proteins, immunological methods will advantageously be used, as described for example in the studies described at the outset on the expression of the MNSOD, TXNRD1 and GPX1 genes.

The skilled worker is able in particular starting from the respective amino acid sequence to produce anti-bodies which are directed against the protein. It is possible for this purpose to use the entire protein or fragments thereof (polypeptides) as immunogen, and to produce, in a manner known per se, polyclonal and monoclonal antibodies and, based thereon by means of recombinant techniques, also humanized antibodies, and fragments thereof.

These antibodies can then be used in particular in quantitative immunoassays and immunoblot techniques, e.g. Western blotting. Both direct and indirect assays are suitable. Competitive immunoassays, i.e. the protein or polypeptide to be detected competes as antigen with labeled antigen for antibody binding, are in particular. Sandwich immunoassays are preferred, i.e. the binding of specific antibodies to the antigen is detected using a second, usually labeled antibody. These assays may be designed to be both homogeneous, i.e. without separation into solid and liquid phase, and heterogeneous, i.e. bound labels are separated from unbound ones, for example by solid phase-bound antibodies. The various heterogeneous and homogeneous immunoassay formats can be assigned, depending on the labeling and method of measurement, to particular classes, for example RIAs (radioimmunoassays), ELISA (Enzyme Linked ImmunoSorbent Assay), FIA (fluorescence immunoassay), LIA (luminescence immunoassay), TRFIA (time-resolved FIA), IMAC (immunoactivation), EMIT (Enzyme Multiplied Immune Test), TIA (turbidimetric immunoassay).

Of the mass spectrometric methods, particular mention should be made of the so-called SELDI method. This comprises the protein mixtures to be investigated initially being trapped on suitable surfaces, e.g. solid support surfaces with affinity for proteins, unwanted substances being removed if necessary from the surfaces, for example by washing with suitable liquids, and subsequently determination being carried out by MALDI-TOF Laser Desorption/Ionization Time-Of Flight Mass Analysis).

The skilled worker is equally able to find nucleic acids which encode this protein or parts thereof and provide suitable means for specific detection thereof.

Thus, methods from the area of nucleic acid analysis which should be particularly mentioned are those based on the specific binding with the nucleic acid to be determined. Included herein is in particular the specific amplification of the nucleic acid to be determined or parts which can be derived therefrom, e.g. determination of mRNA by means of quantitative PCR, and/or specific hybridization thereof onto optionally immobilized probes (especially with the aid of nucleic acid arrays, also called biochips), if necessary after previous specific or nonspecific amplification.

The term "manganese superoxide dismutase (MNSOD for short) according to the invention refers to enzymes which catalyze the decomposition of superoxide free radicals ($O_2^-$) to form hydrogen peroxide ($H_2O_2$). These include in particular the enzymes which constitute enzyme class 1.15.1.1.

Owing to differences in phylogenetic development, there is a certain species-dependent heterogeneity within this group of enzymes. The determination will be directed at the particular MNSOD to be expected in the relevant organism, depending on the individual to be investigated. In a particular embodiment of the present invention, the determination is directed at MNSODs of human origin.

In addition to species-dependent variations, there are also usually for each species polymorphic variants which have different amino acid sequences owing to allelic variation. Variations of this type have already been described (Barra et al. (1984) J. Biol. Chem. 259: 12595-12601; U.S. Pat. No. 5,246,847 (FIG. 1A); U.S. Pat. No. 5,260,204 (claim 1); U.S. Pat. No. 5,985,633 (SEQ ID NO: 1); the 9Ala-9Val polymorphism described in Stoehlmacher J et al. (2002) Oncol. Rep. 9: 235-238). Reference is made to the MNSODs described in these publications in their entirety.

In a particular embodiment of the present invention, the expression analysis is directed at an MNSOD having the amino acid sequence SEQ ID NO:13.

Further useful directions for the MNSOD determination of the invention can also be found by the skilled worker from the nucleic acid sequences indicated in the aforementioned publications. In addition, there are numerous entries in relevant gene databases for MNSOD-encoding nucleic acid sequences, on the basis of which the skilled worker is able to provide suitable means for the sequence-specific detection of these sequences and of expression products which can be derived therefrom. Mention should be made in particular in this connection of MNSOD mRNA which can be isolated from human liver tissue (Accession No. X14322), MNSOD mRNA which can be isolated from human colonic carcinoma (Accession Nos. X59445, X15132, Y00985 and M36693), MNSOD mRNA which can be isolated from human placental tissue (Accession No. X07834), cDNA which can be derived from a human T-cell DNA gene library (Accession No. E01408, cf. also JP 1987289187-A1), and DNAs and RNAs encoding various MNSOD variants (Accession Nos. E03557, E08013 and E08014; cf. also JP 1992117288-A1 and JP 1994245763-A1).

In a further particular embodiment, the sequence-specific detection of MNSOD expression is directed at determination of an mRNA or corresponding cDNA having the sequence SEQ ID NO:14 or a partial sequence thereof.

Specific amplification of this sequence is possible for example using the primer sequences of SEQ ID NO:1 and SEQ ID NO:2. A suitable probe is indicated for example by SEQ ID NO:3. This probe is particularly suitable for the 5'-exonuclease detection using the two afore-mentioned primer sequences.

The term "thioredoxin reductase" (TXNRD for short) according to the invention refers to enzymes which catalyze the NADPH-dependent reduction of thioredoxin-$S_2$ to thioredoxin-$(SH)_2$. These include in particular the enzymes which constitute enzyme class 1.6.4.5.

An additional point is that the thioredoxin reductase family includes a plurality of thioredoxin reductase isoforms of which, besides thioredoxin reductase 1, mention should be made in particular of thioredoxin reductases of type 2 (e.g. α or β), or 3.

Owing to differences in phylogenetic development, there is a certain species-dependent heterogeneity within this group of enzymes. The determination will be directed at the particular TXNRD to be expected in the relevant organism, depending on the individual to be investigated. In a particular embodiment of the present invention, the determination is directed at TXNRDs of human origin.

In addition to species-dependent variations, there are also usually for each species polymorphic variants which have different amino acid sequences owing to allelic variation. Reference is made to the TXNRDs described in these publications in their entirety.

In a particular embodiment of the present invention, the expression analysis is directed at a TXNRD1 having the amino acid sequence SEQ ID NO:15.

Further useful directions for the TXNRD determination according to the invention can be found by the skilled worker from the nucleic acid sequences indicated in the aforementioned publications. In addition, there are numerous entries in relevant gene databases for TXNRD-encoding nucleic acid sequences, on the basis of which the skilled worker is able to provide suitable means for the sequence-specific detection of the sequences and of expression products which can be derived therefrom. Mention should be made in particular in this connection of TXNRD mRNA (Accession Nos. AF106697, S79851, and AF201385), TXNRD mRNA which can be isolated from human placental tissue (Accession No. X9124), TXNRD mRNA which can be isolated from human brain tissue (Accession No. AF208018), TXNRD mRNA which can be isolated from human osteoblasts (Accession No. AJ001050), TXNRD1 mRNA which can be isolated from human large cell lung carcinoma (Accession No. BC018122), TXNRD2α mRNA (Accession No. AB019694) and TXNRD2β mRNA (Accession No. AB019695) which can be isolated from human placental tissue, TXNRDβ mRNA which can be isolated from human melanoma (Accession No. BC007489), TXNRD GRIM-12 mRNA which can be isolated from human breast carcinoma (Accession No. AF077367), TXNRD2 mRNA (Accession No. AF171055) and TXNRD3 mRNA (Accession No. AF133519 and AF171054).

In a further particular embodiment, the sequence-specific detection of TXNRD expression is directed at determination of TXNRD1 expression and in particular of an mRNA or corresponding cDNA having the sequence SEQ ID NO:16 or a partial sequence thereof.

Specific amplification of this sequence is possible for example using the primer sequences SEQ ID NO:4 and SEQ ID NO:5. A suitable probe is indicated for example by SEQ ID NO:6. This probe is particularly suitable for 5'-exonuclease detection using the two primer sequences mentioned above.

The term "glutathione peroxidase" (GPX for short) according to the invention refers to enzymes which—similar to catalases—catalyze the decomposition of hydrogen peroxide ($H_2O_2$) to form water and oxygen. These include in particular the enzymes which constitute enzyme class 1.11.1.9.

An additional point is that the glutathione peroxidase family includes a plurality of glutathione peroxidase isoforms of which, besides glutathione peroxidase 1, mention should particularly be made of the glutathione peroxidases of type 2, 3, 4, 5 or 6.

Owing to differences in phylogenetic development, there is a certain species-dependent heterogeneity within this group of enzymes. The determination will be directed at the particular GPX to be expected in the relevant organism, depending on the individual to be investigated. In a particular embodiment of the present invention, the determination is directed at GPXs of human origin.

In addition to species-dependent variations, there are also usually for each species polymorphic variants which have different amino acid sequences owing to allelic variation. Variations of this type have already been described; e.g. a Pro-Leu amino acid substitution at position 197 (Forsberg L et al. (1999) Hum. Mutat. 14(4):294-300). Reference is made to the GPXs described in these publications in their entirety.

In a particular embodiment of the present invention, the expression analysis is directed at a GPX1 having the amino acid sequence SEQ ID NO:17.

Further useful directions for the GPX determination according to the invention can also be found by the skilled worker from the nucleic acid sequences indicated in the aforementioned publications. In addition, there are numerous entries in relevant gene databases for GPX-encoding nucleic acid sequences, on the basis of which the skilled worker is able to provide suitable means for the sequence-specific detection of these sequences and of expression products which can be derived therefrom. Mention should be made in particular in this connection of human GPX mRNA (Accession No. AF217787), exon 1, 2, and 3 to 5 human GPX DNA (Accession Nos. D16360, D16361 and D16362), GPX mRNA which can be isolated from human placental and fetal liver tissue (Accession No. D00632), GPX mRNA which can be isolated from human liver tissue (Accession Nos. Y00433 and E02175, cf. also JP 1990002362 A1), GPX mRNA which can be isolated from human renal tissue (Accession No. Y13710, Y00369, X13709 and X13430), GPX DNA which can be isolated from human leukocytes (Accession No. Y00483), GPX1 mRNA which can be isolated from human myelocyte leukemia cells (Accession No. M21304), GPX2 DNA which be isolated from human colonic carcinoma (Accession No. X91863), GPX2 mRNA which be isolated from human bladder carcinoma (Accession No. BC005277 and BC016756), GPX2 DNA which be isolated from human fibroblasts (Accession No. AF199441), GPX3 mRNA which be isolated from human placental tissue (Accession No. X58295), GPX3 mRNA which be isolated from human large cell lung carcinoma (Accession No. BC013601), GPX3 mRNA which be isolated from human spleen tissue (Accession No. BC025956), GPX4 mRNA which be isolated from human testicular tissue (Accession No. X71973), GPX4 mRNA which be isolated from human melanoma (Accession No. BC010157) and GPX5 mRNA which be isolated from human epididymis tissue (Accession No. AJ005277).

In a further particular embodiment, the sequence-specific detection of GPX expression is directed at determination of GPX1 expression and in particular of an mRNA or corresponding cDNA having the sequence SEQ ID NO:18 or a partial sequence thereof.

Specific amplification of this sequence is possible for example using the primer sequences SEQ ID NO:7 and SEQ ID NO:8. A suitable probe is indicated for example by SEQ ID NO:9. This probe is particularly suitable for 5'-exonuclease detection using the two primer sequences mentioned above.

The term amplification refers to the multiplication of nucleic acids, i.e. the generation of many copies of particular nucleic acids. The amplification usually proceeds at least linearly and preferably exponentially.

Known amplification methods can be used, which include the polymerase chain reaction (PCR), also carried out in principle as nested PCR, asymmetrical PCR or multiplex PCR, or alternative methods such as the ligase chain reaction (LCR), nucleic acid sequence-based amplification (NASBA), transcription-mediated amplification (TMA) and the like. Certain versions of these techniques and/or combinations with other molecular biology methods may be expedient.

The amplification procedure is preferably based on PCR techniques. For this purpose, usually at least two primers differing in polarity (i.e. at least one pair of primers composed of a forward primer and a reverse primer) are used per template.

In a particular embodiment of the present invention, a pair of specific primers is used per nucleic acid sequence to be determined. An additional possibility is to amplify the total RNA of a sample (cf., for example, Zohlnhöfer D. et al. Circulation 103, 1396-1402, 2001) and subsequently to determine particular RNAs as corresponding cDNAs by specific hybridization.

In a particular embodiment of the present invention, at least one primer which is labeled is used for the amplification. The labeling is used to detect an amplicon into which the labeled primer has been incorporated during the amplification.

The skilled worker is aware of a large number of suitable labels together with relevant detection systems. Fluorescent and chemi- or bioluminescent labels are preferred for reasons of sensitivity and practical handling.

Labeling systems which are suitable in principle are those which can be detected for example spectroscopically, photochemically, biochemically, immunochemically, electrically, optically or chemically. These include both direct labeling systems such as radioactive markers (e.g. $^{32}P$, $^{3}H$, $^{125}I$, $^{35}S$, $^{14}C$), magnetic markers, chromophores, for example UV-, VIS-, or IR-absorbing compounds, fluorophores, chemi- or bioluminescent markers, transition metals, which are usually chelate-bound, or enzymes, e.g. horseradish peroxidase or alkaline phosphatase and the detection reactions coupled thereto, and indirect labeling systems, for example haptens such as biotin or digoxigenin, which can be detected by appropriate detection systems.

Advantageous chromophores have an intense color which is only slightly absorbed by surrounding molecules. Classes of dyes such as quinolines, triarylmethanes, acridines, alizarins, phthaleins, azo compounds, anthraquinones, cyanines, phenazathionium compounds or phenazoxonium compounds may be mentioned here as representative of the wide range of chromophores suitable according to the invention.

Fluorescent labels are advantageous. Strong signals are obtained with little background, high resolution and high sensitivity. It is important according to the invention that one and the same fluorophore may emit a plurality of different radiations depending on the excitation and principle of detection.

Fluorophores can be used alone or in combination with a quencher (e.g. molecular beacons).

Examples of preferred fluorophores are aminomethylcoumarin acetic acid (AMCA, blue) EDANS, BODIPY 493/503; FL; FL Br2; R6G; 530/550; 558/568; TMR 542/574; TR 589/617; 630/650; 650/665, 6-FAM fluorescein (green), 6-OREGON green 488, TET, Cy3 (red), rhodamines (red), 6-JOE, VIC, HEX, 5-TAMRA, NED, 6-ROX, TEXAS Red7 (red), Cy5, Cy5.5, LaJolla Blue, Cy7, Alexa Fluor carboxylic acids, especially of the 647 and 532 type, e.g. as succinimidyl ester, and IRD41.

Particularly preferred fluorophores are Cy5, 5-Tamra and Cy3, and Alexa Fluor carboxylic acids.

Chemiluminescent or bioluminescent labels are likewise advantageous. Preferred labels of this type are based for example on reactions of alkaline phosphatase with dioxetane phosphate (AMPPD) or acridinium phosphate substrates; of horseradish peroxidase with luminol or acridinium ester substrates; of microperoxidases or metal porphyrin systems with luminol; of glucose oxidase, of glucose-6-phosphate dehydrogenase; or of luciferin/luciferase systems.

A label can in principle be introduced in any manner into an amplicon to be detected as long as it permits detection thereof. A distinction can be made in principle between direct and indirect labeling. With direct labeling, the detectable label is incorporated during the amplification. With indirect labeling there is initial incorporation of a primary label which has a certain affinity for the detectable label which is to be added subsequently. The latter procedure is always advantageous when the label to be used might influence the course of the amplification. The indirect procedure is preferred especially in the case of chemi- or bioluminescent labels. Biotin/streptavidin systems in particular have proved to be expedient according to the invention. Accordingly, the labeled primers to be used according to the invention in a particular embodiment of the present invention are labeled with biotin or digoxigenin, preferably at the 5' end.

If at least two different nucleic acids are determined according to the invention, it is usually advantageous to carry out a so-called multiplex amplification, i.e. multiplex PCR in particular. The intention in this case is to subject at least two different nucleic acids to the specific amplification, this taking place in a joint approach. In particular, the multiplex PCR with the aid of at least two, in each case specific, pairs of primers generates just as many different amplicons as long as the appropriate templates are present. It is possible in this case for the primers or pairs of primers to be configured according to the above statements. It is particularly preferred according to the invention for all the primers or pairs of primers to be configured in the same way, so that the generated amplicons can all be treated in an analogous manner in the subsequent method steps. In particular, it is advantageous to be able to detect the amplicons in a joint method step.

In addition, such a multiplex approach may also include further amplification systems which may serve in particular as a control. Thus, it may in particular be desired also to include standardization, mismatch, housekeeping, sample preparation, hybridization or amplification controls.

It is particularly preferred according to the invention to determine the mRNA transcribed by the relevant genes. This may involve mRNA which is already spliced or not yet spliced. The determination is advantageously directed at spliced mRNA.

Ordinarily it is not the mRNA which is directly detected but nucleic acids which be derived therefrom. This applies especially in the case where the detection includes an amplification by PCR. For this purpose, the mRNA is normally initially transcribed into DNA. This is possible for example by reverse transcription, in which case the DNA (cDNA) complementary to the mRNA is generated. Suitable procedures for generating cDNA from mRNA are familiar knowledge in the art.

The resulting cDNA can subsequently be quantified by PCR as a measure of the amount of corresponding mRNA present. Suitable methods for this are also known to the skilled worker (see, for example, Chapter 24.2.5 in Lottspeich F. and Zorbas H. (editors) Bioanalytik, Heidelberg; Berlin: Spektrum, Akad. Verl., 1998, in particular Chapter 21). The technique known by the specialist term of "5'-exonuclease assay" has proved to be particularly effective in this connection. In this case, a labeled probe which is annealed between the two primers onto the nucleic acid sequence to be detected (template), and is degraded during the primer extension through the 5'-3'-exonuclease activity of the polymerase used, is used. The degradation generates a signal. Detection of this signal can be regarded as a measure of the progress of amplification, because the strength of the signal is proportional to the number of amplicons generated, and the time-dependent change in the signal additionally permits conclusions to be drawn about the amount of template. This type of assay is commercially available under the name "TaqMan®".

A further possibility for detecting nucleic acids is provided by techniques based on specific hybridization. These techniques can in principle be applied to the nucleic acids present in the sample, and nucleic acids which can be derived therefrom, it being possible for the nucleic acids, or the nucleic acids which can be derived therefrom, to be subjected to an amplification beforehand, or not.

A large number of different hybridization formats are known in principle to the skilled worker. It is preferred according to the invention to use probes for sequence-specific nucleic acid detection. The procedure for this is usually as follows.

If the nucleic acid to be detected results in double-stranded form, it should be converted into a single-stranded form beforehand. Suitable measures are sufficiently well known to the skilled worker. Thus, double-stranded nucleic acid as generated for example by a PCR can be subjected to denaturing conditions, such as elevated temperature, high ionic strength and/or alkaline pH.

For the hybridization, the hybridization components are allowed to act on one another under conditions which allow duplex formation between nucleic acid sequence to be detected and probe complementary thereto. For example, the immobilized probe is brought into contact with a hybridization mixture which includes the nucleic acid or a nucleic acid which can be derived therefrom and, where appropriate, further customary additions. It is self-evident that parts of the mixture can initially be brought into contact separately from one another with the probe. The hybridization conditions are expediently chosen so that probe and target complementary thereto are able to form stable hybrids. Conditions of relatively low stringency are usually chosen initially, e.g. temperatures of about 20-50° C. and ionic strengths of about 6×SSPE or lower. Subsequent washing is then possible at similar or higher stringency e.g. about 2×SSPE to about 0.1× SSPE at about 30-50° C. It is also possible to have recourse to known agents, e.g. detergents, blocking reagents, denaturing agents, agents which accelerate renaturation and Tm-equalizing agents. Optimization of the hybridization protocol is a matter for the skilled worker.

Immobilized probes are preferably used for the hybridization. For this purpose, the probes are coupled to a support, for example by covalent, adsorptive or by physical/chemical interactions of probe and surface. Suitable methods for achieving an expedient coupling are known to the skilled worker. It is moreover possible for the previously prepared probe to be coupled to the surface, or for the probe to be synthesized in situ on the surface, e.g. by means of photolithographic methods. Coupling via photoactive groups, for example certain anthraquinones, and if necessary a spacer of suitable length and constitution, for example polyethylene glycol with n=2-10 and preferably of about 6 for 8-60 mers, to a reactive surface represents a preferred embodiment. Arrays of immobilized probes are particularly preferred as convenient and efficient format. Reference is made to the statements concerning this in WO 02/18634 in their entirety.

The sequence-specific detection is usually based on determining whether the probe and nucleic acid form a duplex, i.e. hybridize together. The detection according to the invention thus comprises whether a particular target sequence can be found or not (presence or absence). The determination is to take place quantitatively in relation to the expression products of the MNSOD, TXNRD and GPX genes.

The detection usually requires quantification of the nucleic acids which hybridize onto an immobilized probe. The quantification can take place absolutely or relatively. Suitable detection systems are sufficiently well known to the skilled worker. A frequently used possibility consists of introducing labels, e.g. of a radioactive, calorimetric, fluorescent or luminescent nature. These are introduced according to the invention preferably during an amplification which precedes the hybridization—as already explained above—or detected, in the case of indirect labeling after introduction of a primary label such as biotin or digoxigenin (DIG), by adding appropriate markers such as fluorescence-labeled or POD-labeled streptavidin or anti-DIG and, in the case of chemi- or bioluminescence, normally by addition of enzyme substrate solutions or, if substrate molecules such as luminol are used as markers, of enzyme solutions.

The skilled worker is able to choose from the large number of suitable detection systems in particular the photoelectric area sensors described in WO 02/08458, in particular CCD cameras, or the fluorescence scanners described in DE 100 38 080.

c) Evaluation

It is possible with the measurement methods described above to assign to each investigated sample a particular value which characterizes the expression of the investigated gene. It is particularly important according to the invention to determine whether expression in cells of the investigated sample is comparatively elevated, because an elevated MNSOD, TXNRD and GPX expression is relevant to cancer. The evaluation according to the invention therefore usually includes a comparison with cells in which no cancer-associated modification is to be expected (non-cancer cells, normal cells). If the investigation according to the invention is directed for example at cancer cells in body fluids, the cells chosen for comparison will be those normally occurring in this body fluid. In the case of blood, these are in particular the white blood cells which can be obtained for example by density gradient centrifugation (e.g. the buffy coat; the MNC fraction) or be separated by more specific isolation methods (e.g. CD45-positive lymphocytes). These white blood cells can in principle also serve as comparison cells or comparison cell mixtures when investigating body fluids other than blood. A further possibility is for at least one cell-containing fraction of the sample, in particular of the body fluid, to be fractionated by procedures for enriching cancer cells into at least two partial fractions, of which one fraction, optionally enriched in cancer cells, can be used as test cell mixture, and the other fraction, optionally depleted in cancer cells, can be used as comparison cell mixture.

If the investigation according to the invention is carried out on cell mixtures, it is not required for these mixtures to comprise exclusively cancer cells or exclusively non-cancer cells. On the contrary, the important point is the ratio of the cell types to one another in the mixtures. It is sufficient for the method of the invention if the proportion of cancer cells which is to be expected on the basis of the procedures for obtaining the mixtures is significantly higher in the test cell mixture than in the comparison cell mixture. Thus, proportions of cancer cells are perfectly possible in the comparison cell mixture, as long as the proportion of cancer cells in the test cell mixture is sufficiently higher. This can be ensured for example by obtaining the test cell mixture from the comparison cell mixture by procedures for enriching cancer cells.

In a preferred embodiment of the present invention, therefore, a first cell-containing fraction is obtained from the biological sample with enrichment of cancer cells, and the expression of the genes in the cell-containing fraction is determined, a further cell-containing fraction of the biological sample or of a comparable biological sample is prepared, and the expression of the genes in the further cell-containing fraction is determined, and the expression of each gene in the cell-containing fraction is compared with its expression in the further cell-containing fraction. It is advantageous for the comparable biological sample to be derived from the individual whose biological sample is investigated for cancer cells, i.e. a comparison is made with the patient's own non-cancer cells. This is particularly important when the relevant patient has already received therapeutic procedures which have effects on the phenotype and genotype of his cells.

The test principle according to the invention is therefore based on determining whether enrichment of cancer cells is associated with a measurable increase in MNSOD, TXNRD and GPX expression. The ratio of the expression measured in the test cell mixture to the expression measured in the comparison cell mixture is therefore decisive.

It will usually be expedient for validation of a particular test system to fix a particular quotient (limit) above which overexpression is present by definition.

This limit may depend on the cell mixtures used and, in particular, on the obtaining thereof. Thus, it is expedient to carry out a particular embodiment of the method of the invention initially on healthy individuals, i.e. not suffering from cancer, and to fix, with the aid of statistical methods, a suitable limit for the method embodiment used. Thus, it is possible, taking account of statistical significance, to carry out the method on a sufficiently large group of individuals, to form the average from the measured expression ratios, and to fix the limit taking account of the average and of the relevant standard deviation. A limit found in this manner also takes account for example of the cases in which the test cell mixture shows enhanced expression of the measured parameter by comparison with the comparison cell mixture, although the test cell mixture does not contain any cancer cells either. Such cases may occur in particular when the method chosen actually for enrichment of cancer cells leads to enrichment of non-cancer cells which likewise show enhanced expression of the measured parameter. This case was observable for example in relation to GPX1 expression when the white blood cells were subjected to a size- and shape-dependent separation process.

It is moreover usually expedient to relate the values measured on the test cell mixtures and comparison cell mixtures to a standard. Such a standard can be produced for example with the aid of cell lines which show a sufficiently strong expression of the gene expression product to be determined (positive control). For example, the breast carcinoma cell line EFM 192 is suitable as positive control for determining MNSOD and GPX1 expression, and the breast carcinoma cell line MES-SA/Dx5 is suitable for example as positive control for TXNRD1 expression. Further suitable reference cell lines are either known or can be established by the method of the invention, such as, for example, the breast carcinoma cell line BT474.

The investigation according to the invention for cancer cells includes in particular identification thereof and/or characterization thereof.

A further aspect of the present invention is therefore the use of the method of the invention for identifying cancer cells, in particular in early diagnosis of tumors. This is connected in particular with the analytical finding of whether the investigated sample has cancer cells, or the diagnostic finding of whether the individual whose sample has been investigated is suffering from cancer. An elevated expression of at least one MNSOD gene in combination with an elevated expression of at least one TXNRD gene and/or at least one GPX gene, and in particular an elevated expression of at least one MNSOD gene in combination with an elevated expression of at least one TXNRD gene in combination with an elevated expression of at least one GPX gene is to be regarded as an indication of the presence of cancer cells in the investigated samples.

This includes in particular detection of tumor cells from sputum/saliva, especially for early diagnosis of lung tumors; from urine, especially for early diagnosis of prostate and bladder tumors; from stool, especially for early diagnosis of colonic and pancreatic tumors; from blood/bone marrow/lymph, especially for early diagnosis of all disseminating tumors.

One aspect of the present invention is also the use of the method of the invention for characterizing cancer cells, e.g. for classifying tumors and for estimating the risk for the patient. This is connected with prognostic findings about the future course of a cancer, such as the probability (risk) of developing a metastasis or a recurrence, or of surviving a particular time, and therapeutic findings about the efficacy of an applied therapy (therapy monitoring) or findings for choice of the therapy. An elevated expression of at least one MNSOD gene in combination with an elevated expression of at least one TXNRD gene and/or of at least one GPX gene, and in particular an elevated expression of at least one MNSOD gene in combination with an elevated expression of at least one TXNRD gene in combination with an elevated expression of at least one GPX gene is associated with an increased risk of developing a metastasis or a recurrence, and with a reduced probability of surviving a particular time. In order to assess the efficacy of an applied therapy (therapy monitoring), the method of the invention is carried out on at least two different dates, i.e. before and after a particular therapeutic procedure. It is possible to determine by comparing the expression determined before and after the procedure whether the therapeutic procedure has led to a change in the number of cancer cells identifiable by the method of the invention in the sample. A decrease is an indication of the efficacy of the therapeutic procedure. It is possible in this way to assess in particular those therapeutic procedures intended to reduce or eliminate disseminated cancer cells.

In a particular embodiment, the method of the invention is part of a multiparameter investigation which, in addition to the three gene expression analyses of the invention, also includes the investigation of further parameters. In principle, as many parameters as possible should be investigated, so that the only reasons for a restriction are usually those of expediency and practicability. Such multiparameter investigations usually involve investigation of up to 10 000, in particular up to 1000, preferably up to 100, particularly preferably up to 75, 50 or 25 and in particular up to 10, parameters.

The term "parameter" refers in this connection to any biochemical or molecular biological peculiarity of cancer cells and in particular of disseminated cancer cells. Included herein are both therapeutic and diagnostic, especially prognostic, parameters. Genomic parameters, e.g. expressed at the DNA level, are included therein just as much as parameters from the area of expression, e.g. those expressed at the RNA, in particular mRNA, or protein levels. Examples of possible parameters are mutations, insertions, deletions, LOHs, amplifications, aberrations in the set of chromosomes and the like; the expression of splice variants; and the over—and underexpression of certain mRNAs or proteins—and further unusual, in particular cancer-specific, alterations of particular cellular constituents.

Preferred parameters are those relating to qualitative peculiarities of the DNA and/or RNA apparatus. Parameters which should be particularly mentioned in this connection are those relating to cellular properties such as cell division, cell growth, cell-cell interactions, inhibition of tumor suppression and therapy resistances, and especially having oncogenic influences and thus also determining the clinical picture of a cancer. Parameters from the area of DNA recombination, DNA amplification, DNA repair, cell cycling inducers and apoptosis inhibitors are particularly included therein.

Examples which may be mentioned are:
especially oncogenes and tumor suppressor genes, such as p53, genes of the ras family, erb-B2, c-myc, mdm2, c-fos, DPC4, FAP, nm23, RET, WT1 and the like, LOHS, for example in relation to p53, DCC, APC, Rb and the like, and BRCA1 and BRCA2 for hereditary tumors, microsatellite instability of MSH2, MLH1, WT1 and the like; also tumorous RNAs, such as CEA, cytokeratins, e.g. CK20, BCL-2, MUC1, especially tumor-specific splice variants thereof, MAGE3, Muc18, tyrosinase, PSA, PSM, BA46, Mage-1 and the like, or else morphogenic RNAs, such as maspin, HCG, GIP, motilin, hTG, SCCA-1, AR, OR, PR, various hormones and the like;
in addition especially RNAs and proteins which relate to the profile of metastasis, i.e. the expression of angiogenesis, motility, adhesion and matrix degradation molecules such as bFGF, bFGF-R, VEGF, VEGF-Rs such as VEGF-R1 or VEGF-R2, E-cadherin, integrins, selectins, MMPs, TIMPs, SF, SF-R and the like, to the cell cycle profile or proliferation profile, such as cyclines (e.g. the ratio of cyclin D, E and B expressions), Ki67, P120, p21, PCNA and the like, or the apoptosis profile such as FAS (L+R), TNF (L+R), perforin, granzyme B, BAX, bcl-2, caspase 3 and the like.

These and further parameters are described and explained in WO 99/10528, WO 00/06702 and in Giesing M. et al., The International Journal of Biological Markers Vol. 15(1), 94-99, 2000. These statements are incorporated in this description in their entirety by reference.

As indicated above, the present invention also relates to analysis kits for carrying out the method of the invention.
i) at least one means for determining MNSOD gene expression, in particular specific antibodies or, preferably, sequence-specific primers and/or probes like those described above, e.g. primers having the sequences SEQ ID NO:1 and/or SEQ ID NO:2, or probes having the sequence SEQ ID NO:3;
ii) at least one means for determining TXNRD1 gene expression, in particular specific antibodies or, preferably, sequence-specific primers and/or probes like those described above, e.g. primers having the sequences SEQ ID NO:4 and/or SEQ ID NO:5, or probes having the sequence SEQ ID NO:6; and/or
iii) at least one means for determining GPX1 gene expression, in particular specific antibodies or, preferably, sequence-specific primers and/or probes like those described above, e.g. primers having the sequences SEQ ID NO:7 and/or SEQ ID NO:8, or probes having the sequence SEQ ID NO:9; and, where appropriate,
iv) further usual means for carrying out the method of the invention.

Further particular embodiments of kits of the invention are evident from the statements about the method itself.

A further aspect of the present invention relates to a method for the testing and/or functional validation of active substances. For this purpose, the active substance is usually allowed to act ex vivo on disseminated cancer cells which are characterized by elevated expression of the MNSOD, TXNRD1 and/or GPX1 genes, and the response thereof is determined, in particular the expression of the MNSOD, TXNRD1 and/or GPX1 genes resulting after the action of the active substance. As control, the procedures of the method can be carried out in a corresponding manner on cells whose expression of the MNSOD, TXNRD1 and/or GPX1 genes is not elevated. It is usually possible to have recourse to cytobiological test systems known per se. If necessary, disseminated cancer cells can be maintained in culture and suitable bioassays can be carried out. For example, it is possible in this way to test known active substances with an antineoplastic effect and/or active substances employed for adjuvant therapy. It is possible in particular to test targeted active substances. These targets may be according to the invention in particular the MNSOD, TXNRD1 and/or GPX1 genes or the expression products thereof. However, other targets functionally associated with said genes and the expression products thereof are also conceivable and therefore can be validated in relation to MNSOD, TXNRD1 and/or GPX1 gene expression. This is an important aspect of the development of active substances, according to which potential active substances can be selected in a targeted manner—for example by means of screening methods—and subsequently validated.

The purpose of this method for functional validation of active substances is to determine active substance-dependent, molecular and/or morphological alterations in the disseminated cancer cells. If determination of one or more parameters on the disseminated cancer cells reveals a state, after the action of the active substance, which differs from the state which existed before the action of the active substance, the target in relation to the active substance, or the active substance in relation to the target, is functionally validated according to the invention. The functional validation detects in particular a functional association between active substance and target in disseminated cancer cells.

The functional validation of the invention on disseminated cancer cells may where appropriate be based on a functional prevalidation of the target on other cell systems. For example, targets can be cloned and expressed in a manner known per se. Cell systems suitable for this purpose, especially human cell lines, are available to the skilled worker and can be transfected appropriately. Such target-displaying cell systems can be brought into contact in the manner already described above with one or more active substances. This method is also used to establish a molecular and/or morphological action algorithm which can in turn be validated according to the invention on disseminated cancer cells.

This method offers an advantageous basis for the development and testing of targeted active substances. The aiming at targets which have been clinically and functionally validated uniformly on disseminated cancer cells allows active substances to be developed with inclusion of pharmaco- and toxicogenomic aspects to reduce unwanted side effects and a correct stratification of patients, i.e. an—if necessary time-dependent—individualized use of active substances. Considerable savings in costs and time result by comparison with conventional active substance developments.

A further aspect of the present invention relates to the treatment of cancer by modulating the expression of at least two genes which are selected from manganese superoxide dismutase genes, thioredoxin reductase genes and glutathione peroxidase genes.

It is the particular purpose of the treatment according to the invention to reduce the expression of these genes. In this case, the treatment is directed mainly at the cellular constituents of body fluids in which disseminated cancer cells have previously been diagnosed. It is to be assumed that the phenotype of a majority of the disseminated cancer cells present in an individual is influenced by the treatment according to the invention so that the ability of the disseminated cancer cells to survive is reduced.

Without being tied to a particular mechanism, such an effect of treatment can be explained by the disseminated cancer cells losing a protective mechanism which is mediated by overexpression of one or more of the above genes, or being less adapted to the conditions prevailing in the particular body fluid, so that enhanced elimination of the disseminated cancer cells occurs.

An advantageous treatment variant of the invention is directed at modulation of MNSOD expression in combination with modulation of TXNRD and/or GPX expression. Modulation of MNSOD, TXNRD and GPX expression is particularly advantageous.

Methods and means for modulating the expression of particular genes are known in principle. In particular, gene expression can be reduced for example at the RNA level with the aid of specific antisense molecules. At the protein level, expression is reduced with the aid of specific binding partners which have a sufficient affinity for the expressed proteins and impair the function thereof. These include, for example, specific antibodies, but also low molecular weight compounds which, in the present case, can be developed on the basis of the reactions catalyzed by the enzymes and, in particular, the substrates converted. Accordingly, it is possible in particular to employ inhibitors of MNSOD, TXNRD and/or GPX activity.

An effective amount of a combination of active substances which is able to reduce the expression of at least two genes selected from MNSOD, TXNRD and GPX genes, and to eliminate disseminated cancer cells in a treated individual is therefore administered according to the invention to the individual to be treated.

The present invention therefore also relates to the use of a combination of appropriate active substances for providing a pharmaceutical composition for the treatment of cancer. In this connection, this combination of active substances can be administered in the form of an appropriate cocktail of active substances or in the form of individual active substances at different times, for example alternately at different times of day or sequentially, where the active substances are usually prepared as pharmaceutical composition in accordance with the rules of pharmaceutical practice.

EXEMPLARY EMBODIMENTS

Description of the Figure

FIG. 1 shows the evaluation, plotted as bar diagram, of a CCD contact exposure image of the fluorescence radiation emitted from an array populated with the specified gene-specific probes after hybridization with cDNA single-stranded fragments obtained from cells in the blood of a tumor patient.

Samples

The following samples are used for the investigations described below:

Blood from 9 healthy donors and 47 tumor patients; breast carcinoma cell line BT474 (reference cell line for MNSOD, TXNRD1 and GPX1 overexpression)

Tumor Cell Isolation (Cancer Cell Fraction C)

10 ml of heparinized blood are centrifuged (400 g; 10 min; RT). The supernatant plasma is removed. The pelleted cells are taken up in 12 ml of PBS. After density gradient centrifugation (Nycodenz 1.077; 800 g; 30 min, RT) the interphase cells (essentially mononuclear cells, MNC fraction for short) are removed and washed 2× in 10 ml of PBS (1 mM EDTA) 9400 g; 10 min; 4° C.). The MNC fraction is taken up in 10 ml of this cell mixture is removed as possible references (comparative fraction A'). The remaining 9 ml of cell mixture are passed via a column through a screen woven from polyester filaments with a 20 µm mesh width (marketed by SEFAR AG, Rüschlikon, Switzerland), and the flow through from the screen is collected as possible reference (comparative fraction B'). The column is washed 5× with 10 ml of PBS (1 mM EDTA) each time. The screen is removed, inverted and incubated in a reaction vessel with 0.7 ml of Trizol® (5 min; RT). The screen is placed above the Trizol® solution in the reaction vessel and centrifuged (200 g; 30 s; RT). The dry screen is removed and the Trizol® solution (cancer cell fraction C) passed on for further RNA isolation.

An alternative possibility to incubation of the screen in Trizol® is for the screen to be removed from the column, inverted and transferred into PBS (1 mM EDTA, 0.5% BSA), the cells can be pelleted by centrifugation (400 g; 10 min, 4° C.) and passed on for further RNA isolation.

Normal Cell (Non-cancer Cell) Isolation (Comparative Fractions A and B)

CD45-positiven lymphocytes are isolated as comparative fractions by removing in each case ¹/₁₀ of the MNC fraction before (fraction A') and after (fraction B') the screening process. They are transferred into a reaction vessel containing 1 ml of PBS (0.5% BSA, 100 µg hu-IgG). 50 µl of washed anti-CD45 microbeads are added thereto. The mixture is rotated at 4° C. for 20 min. The reaction vessel is then positioned on a magnetic strip in such a way that the microbeads (bound to CD45-positive MNCs) are pelleted on the vessel wall. A pure population of CD45-positive lymphocytes is obtained by washing the bead-cell aggregates three times and can then, dissolved in Trizol®, be passed on for RNA isolation. CD45 isolates of the MNC fraction before and after the screening process are referred to as comparative fraction A and B, respectively.

RNA Isolation

The RNA is extracted and purified from the above cell lines in a manner known per se, e.g. with the aid of suitable kits as obtainable from commercial suppliers, e.g. from Qiagen and GIBCO-BRL.

mRNA Expression Analysis

The amounts of expressed mRNA are determined by quantitative RT-PCR. The PCR format is based on the 5'-exonuclease assay known per se (e.g. TaqMan®) and is suitable for use on the TaqMan® 7700 sequence detector from Applied Biosystems (ABI).

The following reagents are employed:
a) Reverse transcription (RT)
5× first strand buffer (from Boehringer)
0.1 M dithiothreitol (DTT)
RNA guard 38950 U/ml (from Pharmacia)
random hexamers 500 µg/ml (from Promega)
dNTPs each 20 mM (from Pharmacia)
M-MLV 200 U/µl (from Gibco)
b) PCR
10×TaqMan® buffer (from Perkin Elmer (PE))
$MgCl_2$ 25 mM (PE)
dNTP mix (0.75 µl of each; 2.5 mM)
ROX solution (100×) (TIB)

Amplitaq® Gold (PE) (for hot start method)

The reagents mentioned are present in the Perkin Elmer TaqMan® PCR core reagent kit.

To carry out the RT-PCR:

1. Reverse Transcription (RT)

Firstly an RT mix composed of 2.35 µl of $H_2O$, 4 µl of 5× first strand buffer, 2 µl of 0.1 M DTT, 0.15 µl of RNA guard (38950 U/ml), 0.5 µl of random hexamers (500 µg/ml), 0.5 µl of dNTP mix, 20 mM each, and 0.5 µl of M-MLV (200 U/µl) is prepared.

10 µl of RNA (approx. 1 µg from RNA isolation) are denatured at 70° C. for 1 min, immediately placed on ice and cooled for 3 min, and subsequently mixed with 10 µl of RT mix free of air bubbles, incubated initially at 37° C. for 60 min and then at 95° C. for 3 min, immediately placed on ice and cooled for 3 min.

This reaction mixture comprising the reverse transcript (cDNA) is either subjected directly to the PCR or frozen at −20° C.

2. PCR

Firstly a PCR premix composed of 28.5 µl of $H_2O$, 5.0 µl of buffer (PE), 6 µl of ROX solution (100×) (TIB), 6.0 µl of $MgCl_2$ (25 mM), 3.0 µl of dNTP mix (0.75 µl of each; 2.5 mM), 1.0 µl of primer (sense; 20 pmol/µl), 1.0 µl of primer (antisense; 20 pmol/µl), 0.5 µl of probe (20 pmol/µl) and 0.5 µl of Amplitaq Gold (PE 5 U/µl) is prepared.

Special reaction vessels are required for detecting the PCR products on the TaqMan® 7700 sequence detector. The PE optical tubes in combination with the PE optical caps are suitable. 47 µl of PCR premix and 3 µl of cDNA solution are employed per tube.

A 2-step method with the following thermocycling conditions is then chosen for the amplification:

95° C. 10 min hot start activation
95° C. 30 sec
60° C. 60 sec
20° C. indefinitely number of cycles: 45

2.1 Determination of Manganese Superoxide Dismutase mRNA (MNSOD mRNA)

The following MNSOD-specific primers and probes are used (MNSOD, SOD2; accession No.: M36693):

```
sense:
5'-GTCACCGAGGAGAAGTACCAGG-3'         (SEQ ID NO: 1)

antisense:
5'-GGGCTGAGGTTTGTCCAGAA-3'           (SEQ ID NO: 2)

probe:
5'-CGTTGGCCAAGGGAGATGTTACAGCCC-3'    (SEQ ID NO: 3)
```

Size of the PCR product: 131 bp.

2.2 Determination of Thioredoxin Reductase 1 mRNA (TXNRD1 mRNA)

The following TXNRD1-specific primers and probes are used (TXNRD1; accession No.: X91247 cDNA):

```
sense:
5'-GGAGGGCAGACTTCAAAAGCTAC-3'        (SEQ ID NO: 4)

antisense:
5'-ACAAAGTCCAGGACCATCACCT-3'         (SEQ ID NO: 5)

probe:
5'-TTGGGCTGCCTCCTTAGCAGCTGCCA-3'     (SEQ ID NO: 6)
```

Size of the PCR product: 158 bp.

2.3 Determination of Glutathione Peroxidase mRNA (GPX1 mRNA)

The following GPX1-specific primers and probes are used (GPX1; accession No.: M21304):

```
sense:
5'-CTCGGCTTCCCGTGCAA-3'              (SEQ ID NO: 7)

antisense:
5'-TGAAGTTGGGCTCGAACCC-3'            (SEQ ID NO: 8)

probe:
5'-AGTTTGGGCATCAGGAGAACGCCAAGAA-3'   (SEQ ID NO: 9)
```

Size of the PCR product: 109 bp.

2.4 Determination of Glyceraldehyde-3-phosphate Dehydrogenase mRNA (GAPDH mRNA)

The following GAPDH-specific primers and probes are used (GAPDH; accession No. X01677):

```
sense:
5'-TGCTGATGCCCCCATGTTC-3'            (SEQ ID NO: 10)

antisense:
5'-GGCAGTGATGGCATGGACTG-3'           (SEQ ID NO: 11)

probe:
5'-TCAAGATCATCAGCAATGCCTCCTGCA-3'    (SEQ ID NO: 12)
```

Size of the PCR product: 174 bp.

3. Evaluation

For the evaluation, the ratio of cell equivalents of the mRNA to be determined to cell equivalents of GAPDH mRNA is found for each of the fractions A or A' and C, and the ratio of the resulting quotients is found in turn. Overexpression of the relevant mRNA is present if the ratio of the fraction C quotient to the fraction A quotient is more than a limit which is to be defined.

The cell equivalents are based on a cell standard. This cell standard is produced by mRNA being extracted from a known number of cells (e.g. $2 \times 10^6$) of a cell suspension of a carcinoma cell line which expresses the respective parameter (cell line BT474 for MNSOD, GPX1 and TXNRD1) in the manner described above, and transcribed into cDNA. This cDNA is included in each quantitative analysis in the form of serial dilutions (e.g. 6 dilution levels) and serves as reference system.

Results:

Example 1

Healthy Donors

The amounts of MNSOD, TXNRD1 and GPX1 mRNA determined in the isolated cells (fraction C) for healthy donors (number N) are indicated in table 1, specifically as ratio to the amounts of corresponding mRNAs in the comparative cell fraction (fraction A).

TABLE 1

MNSOD, TXNRD1 and GPX1 mRNA expression in the blood of healthy donors

|  | N | Average | Standard deviation | Limit |
|---|---|---|---|---|
| MNSOD | 9 | 0.9300 | 0.2891 | 1.2 |
| TXNRD1 | 9 | 0.9133 | 0.4166 | 1.3 |
| GPX1 | 8 | 3.6888 | 1.5533 | 5.2 |

The cells isolated from blood show a slightly elevated GPX1 expression. The expression of MNSOD and TXNRD1 is unchanged relative to the comparative cell fraction, that is the lymphocytes.

For the subsequent assessment of the levels of expression measured in tumor patients, the levels regarded as positive are those which exceed the average level plus standard deviation. These levels are indicated as limit in table 1.

Example 2

Tumor Patients

A number of tumor patients with different tumors are included in the investigation. The tumors had been diagnosed by various other medical methods.

1. Sensitivity

The number of cases among tumor patients (number N) in which the expression of MNSOD, TXNRD1 and GPX1 mRNA is elevated (positive) in the isolated cells (fraction C) in relation to the cells of the complete cell fraction (fraction A') is indicated below, grouped according to type of tumor.

| MNSOD | | |
|---|---|---|
| Investigations | | N = 93 |
| Patients | | N = 90 |
| of which | breast | 41 (40 positive) |
| | colon | 8 (8 positive) |
| | prostate | 8 (7 positive) |
| | ovary | 8 (5 positive) |
| | lung | 5 (2 positive) |
| | bladder | 4 (3 positive) |
| | liver | 2 (1 positive) |
| | thyroid | 2 (2 positive) |
| | others | 12 (10 positive) |
| | | → 78/90 = 87% POSITIVE |
| TXNRD1 | | |
| Investigations | | N = 93 |
| Patients | | N = 90 |
| of which | breast | 41 (31 positive) |
| | colon | 9 (6 positive) |
| | prostate | 8 (6 positive) |
| | ovary | 7 (3 positive) |
| | lung | 5 (1 positive) |
| | bladder | 4 (3 positive) |
| | liver | 2 (1 positive) |
| | thyroid | 2 (1 positive) |
| | others | 12 (8 positive) |
| | | → 60/90 = 67% POSITIVE |
| GPX1 | | |
| Investigations | | N = 89 |
| Patients | | N = 86 |
| of which | breast | 40 (25 positive) |
| | colon | 8 (6 positive) |
| | prostate | 7 (5 positive) |
| | ovary | 7 (3 positive) |
| | lung | 4 (2 positive) |
| | bladder | 4 (2 positive) |
| | liver | 2 (2 positive) |
| | thyroid | 2 (2 positive) |
| | others | 12 (6 positive) |
| | | → 53/86 = 62% POSITIVE |
| MNSOD and TXNRD1 and GPX1 | | |
| Investigations | | N = 88 |
| Patients | | N = 85 |
| | 0 positive | 6/85 = 7% |
| | 1 positive | 9/85 = 11% |
| | 2 positive | 33/85 = 39% |
| | 3 positive | 37/85 = 44% |
| | | → at least 1 gene POSITIVE in 93% |

A detection directed at determination of all 3 parameters therefore has a sensitivity of 93%, while the sensitivity of the individual detections is 87, 67 and 62%, respectively.

2. Correlation with One Another

In addition to the sensitivity of each individual parameter, it emerges that in 74% (58/78) of the cases in which MNSOD expression is elevated there is also an observable enhancement of TXNRD1 expression (Pearson's rho correlation coefficient is 0.75). Moreover some, namely 65% (49/75), of the patients with elevated MNSOD expression also have elevated GPX1 expression (compare tables 2a, b, c: correlation analysis of TXNRD1 and GPX1 relative to MNSOD and of GPX1 relative to TXNRD1).

The correlation between an elevated MNSOD expression and an elevated TXNRD1 expression in disseminated cancer cells was not to be expected because the two enzymes have different functions.

TABLE 2a

Correlation of TXNRD1 relative to MNSOD

| | MNSOD negative | | MNSOD positive | |
|---|---|---|---|---|
| TXNRD1 negative | 10/11 | 91% | 20/78 | 26% |
| TXNRD1 positive | 1/11 | 9% | 58/78 | 74% |

$p = 0.0001$ (Pearson's test)

TABLE 2b

Correlation of GPX1 relative to MNSOD

| | MNSOD negative | | MNSOD positive | |
|---|---|---|---|---|
| GPX1 negative | 7/11 | 64% | 26/75 | 35% |
| GPX1 positive | 4/11 | 36% | 49/75 | 65% |

$p = 0.10$ (Pearson's test)

TABLE 2c

Correlation of GPX1 relative to TXNRD1

| | TXNRD1 negative | | TXNRD1 positive | |
|---|---|---|---|---|
| GPX1 negative | 12/27 | 44% | 20/58 | 34% |
| GPX1 positive | 15/27 | 56% | 38/58 | 66% |

$p = 0.38$ (Pearson's test)

3. Correlation with bcl-2 Overexpression

It also emerges that in 100% (5/5) of the cases in which TXNRD1 expression is elevated there is an observable enhancement of bcl-2 expression (Pearson's rho correlation coefficient is 0.32, and that of Spearman is 0.58; compare tables 3a, b, c: correlation analysis of MNSOD, TXNRD1 and GPX1 relative to bcl-2).

This shows that an elevated TXNRD1 expression is involved in the apoptosis blockade associated with elevated bcl-2 expression.

TABLE 3a

Correlation of MNSOD relative to bcl-2

|  | bcl-2 negative | | bcl-2 positive | |
|---|---|---|---|---|
| MNSOD negative | 9/41 | 22% | 0/5 | 0% |
| MNSOD positive | 32/41 | 78% | 5/5 | 100% | p = 0.57 (Pearson's test)

TABLE 3b

Correlation of TXNRD1 relative to bcl-2

|  | bcl-2 negative | | bcl-2 positive | |
|---|---|---|---|---|
| TXNRD1 negative | 20/41 | 49% | 0/5 | 0% |
| TXNRD1 positive | 21/41 | 51% | 5/5 | 100% | p = 0.06 (Pearson's test)

TABLE 3c

Correlation of GPX1 relative to bcl-2

|  | bcl-2 negative | | bcl-2 positive | |
|---|---|---|---|---|
| GPX1 negative | 10/39 | 26% | 3/5 | 60% |
| GPX1 positive | 29/39 | 74% | 2/5 | 40% | p = 0.14 (Pearson's test)

4. Correlation with Tumor Patients

A comparison between the healthy donors and some of the tumor patients (tables 4a-c) shows that there is a surprisingly clear correlation between the measured elevated expression of the MNSOD, TXNRD1 and GPX1 genes and the tumor patients.

TABLE 4a

Comparison between healthy donors and tumor patients in relation to MNSOD expression

|  | Healthy | TUMOR |
|---|---|---|
| N | 9 | 43 |
| Average | 0.93 | 4.82 |
| Median | 1.01 | 3.62 |

Wilcoxon p = 0.0004
Median p = 0.001

TABLE 4b

Comparison between healthy donors and tumor patients in relation to TXNRD1 expression

|  | Healthy | TUMOR |
|---|---|---|
| N | 9 | 44 |
| Average | 0.91 | 2.18 |
| Median | 0.97 | 1.72 |

Wilcoxon p = 0.02
Median p = 0.01

TABLE 4c

Comparison between healthy donors and tumor patients in relation to GPX1 expression

|  | Healthy | TUMOR |
|---|---|---|
| N | 8 | 38 |
| Average | 3.69 | 18.98 |
| Median | 2.88 | 13.09 |

Wilcoxon p = 0.0006
Median p = 0.002

5. Correlation with Recurrences

A further comparison within the group of tumor patients between those who have had a recurrence and those who have had no recurrence shows that there is likewise a surprisingly clear correlation between the measured elevated expression of the MNSOD, TXNRD1 and GPX1 genes and the recurrences. This applies to all the tumors investigated (tables 5a-c) and in particular to patients with carcinoma of the breast (tables 6a-c). A surprising advantage of the method of the invention is that at least 2, and in particular all 3, parameters correlate better with the clinical course of a cancer than one parameter alone (tables 7a, b).

TABLE 5a

Comparison between tumor patients without recurrence and those with recurrence in relation to MNSOD expression

|  | No recurrence | Recurrence |
|---|---|---|
| N | 23 | 14 |
| Average | 3.12 | 6.17 |
| Median | 2.78 | 5.43 |

Wilcoxon p = 0.02
Median p = 0.005

TABLE 5b

Comparison between tumor patients without recurrence and those with recurrence in relation to TXNRD1 expression

|  | No recurrence | Recurrence |
|---|---|---|
| N | 23 | 14 |
| Average | 1.48 | 2.32 |
| Median | 1.17 | 2.09 |

Wilcoxon p = 0.05
Median p = 0.14

TABLE 5c

Comparison between tumor patients without recurrence and those with recurrence in relation to GPX1 expression

|  | No recurrence | Recurrence |
|---|---|---|
| N | 20 | 14 |
| Average | 13.01 | 23.49 |
| Median | 9.20 | 15.66 |

Wilcoxon p = 0.05
Median p = 0.04

TABLE 6a

Comparison between patients with carcinoma of the breast without recurrence and those with recurrence in relation to MNSOD expression

|  | No recurrence | Recurrence |
|---|---|---|
| N | 12 | 4 |
| Average | 2.92 | 8.71 |
| Median | 2.73 | 6.66 |

Wilcoxon p = 0.03
Median p = 0.03

TABLE 6b

Comparison between patients with carcinoma of the breast without recurrence and those with recurrence in relation to TXNRD1 expression

|  | No recurrence | Recurrence |
|---|---|---|
| N | 12 | 4 |
| Average | 1.53 | 2.95 |
| Median | 1.43 | 2.84 |

Wilcoxon p = 0.06
Median p = 0.26

TABLE 6c

Comparison between patients with carcinoma of the breast without recurrence and those with recurrence in relation to GPX1 expression

|  | No recurrence | Recurrence |
|---|---|---|
| N | 11 | 4 |
| Average | 11.12 | 19.17 |
| Median | 9.10 | 15.66 |

Wilcoxon p = 0.13
Median p = 0.02

TABLE 7a

Comparison between patients with carcinoma of the breast without recurrence and those with recurrence in relation to MNSOD, TXNRD1 and GPX1 expression

|  | No recurrence |  | Recurrence |  |
|---|---|---|---|---|
| 0 | 0/18 | 0% | 0/7 | 0% |
| 1 | 2/18 | 11% | 0/7 | 0% |
| 2 | 8/18 | 44% | 3/7 | 43% |
| 3 | 8/18 | 44% | 4/7 | 57% |

TABLE 7b

Comparison between tumor patients without recurrence and those with recurrence in relation to MNSOD, TXNRD1 and GPX1 expression

|  | No recurrence |  | Recurrence |  |
|---|---|---|---|---|
| 0 | 1/28 | 4% | 3/29 | 10% |
| 1 | 4/28 | 14% | 2/29 | 7% |
| 2 | 11/28 | 39% | 9/29 | 31% |
| 3 | 12/28 | 43% | 15/29 | 52% |

6. Correlation with DNA Aberrations

The occurrence of DNA aberrations, i.e. genomic imbalances (G.I.) (cf. Giesing M, et al. Int J Biol Markers, 94-99, 2000) in the isolated cells also correlates clearly with elevated expression of the MNSOD, TXNRD1 and GPX1 genes, as proved by the results shown in tables 8a-d. The number of genomic imbalances correlates with the number of overexpressed genes selected from MNSOD, TXNRD1 and GPX1.

TABLE 8a

Comparison between the absence and the occurrence of genomic imbalances in relation to MNSOD overexpression

|  | 1 G.I. |  | $\geq$2 G.I. |  |
|---|---|---|---|---|
| SOD > 1.2 | 16/19 | 84% | 8/8 | 100% |

TABLE 8b

Comparison between the absence and the occurrence of genomic imbalances in relation to TXNRD1 overexpression

|  | 1 G.I. |  | $\geq$2 G.I. |  |
|---|---|---|---|---|
| TXNRD1 > 1.3 | 12/19 | 63% | 5/9 | 56% |

TABLE 8c

Comparison between the absence and the occurrence of genomic imbalances in relation to GPX1 overexpression

|  | 1 G.I. |  | $\geq$2 G.I. |  |
|---|---|---|---|---|
| GPX1 > 5.2 | 11/17 | 65% | 8/8 | 100% |

TABLE 8d

Comparison between the absence and the occurrence of genomic imbalances in relation to MNSOD, TXNRD1 and GPX1 overexpression

|  | 1 G.I. |  | $\geq$2 G.I. |  |
|---|---|---|---|---|
| 0 | 0/17 | 0% | 0/7 | 0% |
| 1 | 2/17 | 12% | 0/7 | 0% |
| 2 | 8/17 | 53% | 2/7 | 29% |
| 3 | 8/17 | 35% | 5/7 | 71% | mRNA Expression Analysis According to the Invention Using Biochips mRNA Total Amplification The RNA amplification takes place as described in Zohlnhöfer D, et al. Circulation 103, 1396-1402, 2001.

Chip Design

Besides various tumor-relevant gene-specific probes, also integrated on the chip are probes for quantifying MNSOD, GPX2, GPX3 and TXNRD expression.

The following MNSOD-, GPX2-, GPX3- and TXNRD-specific probes are used:

MNSOD:
(SEQ ID NO: 19)
GAACAACAGGCCTTATTCCACTGCTGGGGATTGATGTGTGGGAGCACGCT
TACTACCTTC

TXNRD1:
(SEQ ID NO: 20)
CGTGTTGTGGGCTTTCACGTACTGGGTCCAAATGCTGGAGAAGTTACACA
AGGCTTTGCA

GPX2:

(SEQ ID NO: 21)
TACAGCCGCACCTTCCCAACCATCAACATTGAGCCTGACATCAAGCGCCT
CCTTAAAGTT

GPX3:

(SEQ ID NO: 22)
CTCTTCTGGGAACCCATGAAGGTTCACGACATCCGCTGGAACTTTGAGAA
GTTCCTGGTG

Production of the Oligonucleotide Arrays
Production of the Probes
a) Oligonucleotides (60-mers)

The oligonucleotides are produced in a manner known per se by solid-phase synthesis with the phosphoramidite method. Oligonucleotides which are coupled via the 3'-OH to the solid phase and have DMTr-protected 5'-OH and the above sequence are synthesized.

b) Quinone-spacer construct

This is synthesized in a manner known per se from anthraquinone-2-carboxylic acid, mono-Boc-1, 3-propane-diamine and hexaethylene glycol.

c) Quinone-spacer-oligonucleotide construct

After assembly of the above sequences, the DMTr protective group at the 5' end is again removed under acidic conditions with $ZnBr_2$, and the free 5'-OH is reacted with the 2-cyanoethyl-N,N-diisopropylchloro-phosphoramidite-activated quinone-spacer construct.

The quinone derivatives synthesized in this way therefore have a structure of the general formula AQ-CO—NH—$(CH_2)_3$—NH—$(CH_2)2$—$(OCH_2CH_2)_5$—O—$PO_2$-5' (SEQ ID NO:19-22)-3'.

The other cancer-relevant gene-specific probes are also produced in an analogous manner.

Coupling of the Probes to the Array Surface

An aqueous solution (2 mM calcium chloride; 1% by vol. 1-propanol) of each desired quinone derivative (10 μM) is applied using a piezodispenser (1-channel; Genesis NPS 100/4 with Active Tip M, TECAN AG, Hombrechtikon, CH) in a 400 μm grid on polycycloolefin (Zeonex 480R; Zeon). The drop size is about 0.5 nl. After the spots have dried, the support is irradiated with UV light for 1 min. The support is then washed and dried in air at room temperature. The diameters of the resulting spots are about 120 to 180 μm.

Hybridization

The mixtures obtained from the RNA amplification are diluted in a suitable manner with 2×SSPE buffer and pipetted onto the array. It is incubated at 60° C. for 16 hours. After two washing steps with 1×SSPE buffer at 60° C., Cy5-streptavidin (Amersham Pharmacia Biotec) is added and incubated at room temperature for 15 min.

Evaluation of the Array

The fluorescence is determined using a CCD camera scanner.

Example 3

Tumor Patients

FIG. 1 shows a CCD contact exposure image of the fluorescence radiation emitted from the array after hybridization with cDNA single-stranded fragments which were generated in the manner described above by means of mRNA total amplification from the tumor cell fraction C and the comparative cell fraction A'.

Overexpression of MNSOD and GPX2 in the tumor cell fraction is clearly evident. The measurement underlines the increased sensitivity and specificity of the detection method of the invention compared with other tumor cell-detecting genes.

The invention claimed is:

1. A method for determining whether disseminated cancer cells are present in a blood sample from a human subject having or suspected of having cancer, wherein the method comprises:
   (a) obtaining a blood sample from a human subject having or suspected of having cancer, collecting from the blood sample a cell fraction that comprises mononuclear cells (MNC fraction), removing a fraction of the MNC fraction to obtain test fraction A', passing the remaining MNC fraction through a screen with a mesh or pore width of 17-27 µm, and collecting cells from the screen to obtain test fraction C;
   (b) isolating mRNA from test fraction A' and test fraction C to obtain mRNA samples;
   (c) measuring in each of the mRNA samples obtained in step (b) the expression level of manganese superoxide dismutase (MNSOD) mRNA that encodes a protein having the amino acid sequence of SEQ ID NO:13 or an allelic variant thereof, thioredoxin reductase (TX-NRD1) mRNA that encodes a protein having the amino acid sequence of SEQ ID NO:15 or an allelic variant thereof, and glutathione peroxidase (GPX1) mRNA that encodes a protein having the amino acid sequence of SEQ ID NO:17 or an allelic variant thereof, wherein said measuring is by reverse transcription into cDNA and PCR;
   (d) determining the expression ratio of MNSOD, TXNRD1, and GPX1 from test fraction C to test fraction A'; and
   (e) comparing the expression ratio for each of MNSOD, TXNRD1, and GPX1 determined in step (d) to a control limit for expression for each of MNSOD, TXNRD1, and GPX1 in blood samples of healthy human subjects,
   and wherein an expression ratio determined in step (d) higher than the control limit of expression of at least one of MNSOD, TXNRD1 and GPX1 indicates the presence of disseminated cancer cells in the blood sample from a human subject having or suspected of having cancer.

2. The method of claim 1, wherein the presence of disseminated cancer cells in the blood sample from a human subject having or suspected of having cancer indicates the presence of a tumor.

3. The method of claim 1, wherein the presence of disseminated cancer cells in the blood sample from a human subject having or suspected of having cancer indicates a risk to develop a metastasis or a recurrence.

4. The method of claim 1, wherein the screen has a mesh or pore width of about 20 µm.

5. The method of claim 1, wherein the cDNA obtained by reverse transcription comprises the nucleotide sequences of SEQ ID NO:1 and 2 for MNSOD mRNA; SEQ ID NO:4 and 5 for TXNRD1 mRNA, and SEQ ID NO:7 and 8 for GPX1 mRNA.

6. The method of claim 5, wherein the control limit for expression has been determined by performing the following steps:
   (f) obtaining blood samples from healthy human subjects not suffering from cancer, collecting a cell fraction that comprises mononuclear cells (MNC fraction) from the blood samples, removing a fraction of the MNC fraction to obtain reference fraction A', passing the remaining MNC fraction through a screen with a mesh or pore width of 17-27 µm mesh, and collecting cells from the screen to obtain reference fraction C;
   (g) optionally isolating CD45-positive lymphocytes from reference fraction A' to obtain reference fraction A,
   (h) isolating mRNA from reference fraction A' or A and reference fraction C to obtain mRNA samples;
   (i) measuring in each of the mRNA samples obtained in step (h) the expression level of MNSOD mRNA that encodes a protein having the amino acid sequence of SEQ ID NO:13 or an allelic variant thereof, TXNRD1 mRNA that encodes a protein having the amino acid sequence of SEQ ID NO:15 or an allelic variant thereof, and GPX1 mRNA that encodes a protein having the amino acid sequence of SEQ ID NO:17 or an allelic variant thereof, wherein said measuring is by reverse transcription into cDNA and PCR; and
   (j) determining the average for the expression ratio of MNSOD, TXNRD1, and GPX1 from reference fraction C to reference fraction A' or A, and determining a control limit for expression.

7. The method of claim 5, wherein the control limit for expression has been determined by performing the following steps:
   (f) obtaining blood samples from healthy human subjects not suffering from cancer, collecting a cell fraction that comprises mononuclear cells (MNC fraction) from the blood samples, removing a fraction of the MNC fraction to obtain reference fraction A', passing the remaining MNC fraction through a screen with a mesh or pore width of 17-27 µm mesh, and collecting cells from the screen to obtain reference fraction C;
   (g) isolating CD45-positive lymphocytes from reference fraction A' to obtain reference fraction A,
   (h) isolating mRNA from reference fraction A and reference fraction C to obtain mRNA samples;

(i) measuring in each of the mRNA samples obtained in step (h) the expression level of MNSOD mRNA that encodes a protein having the amino acid sequence of SEQ ID NO:13 or an allelic variant thereof, TXNRD1 mRNA that encodes a protein having the amino acid sequence of SEQ ID NO:15 or an allelic variant thereof, and GPX1 mRNA that encodes a protein having the amino acid sequence of SEQ ID NO:17 or an allelic variant thereof, wherein said measuring is by reverse transcription into cDNA and PCR; and (j) determining the average and standard deviation for the expression ratio of MNSOD, TXNRD1, and GPX1 from reference fraction C to reference fraction A, and determining a control limit for expression.

* * * * *